(12) United States Patent
Nakatsura et al.

US009404925B2

(10) Patent No.: US 9,404,925 B2
(45) Date of Patent: Aug. 2, 2016

(54) CANCER ANTIGEN AND USE THEREOF

(75) Inventors: Tetsuya Nakatsura, Kumamoto (JP); Yasuharu Nishimura, Kumamoto (JP)

(73) Assignee: MEDINET CO., LTD., Kanagawa (JP)

( * ) Notice: Subject to any disclaimer, the term of this patent is extended or adjusted under 35 U.S.C. 154(b) by 533 days.

(21) Appl. No.: 12/155,864

(22) Filed: Jun. 11, 2008

(65) Prior Publication Data

US 2009/0074800 A1    Mar. 19, 2009

Related U.S. Application Data

(62) Division of application No. 10/525,831, filed as application No. PCT/JP03/11049 on Aug. 29, 2003, now abandoned.

(30) Foreign Application Priority Data

Aug. 30, 2002   (JP) .................................. 2002-255668
Nov. 25, 2002   (JP) .................................. 2002-341168

(51) Int. Cl.
*A61K 38/17*    (2006.01)
*A61K 39/39*    (2006.01)
*C07K 7/06*     (2006.01)
*C07K 14/47*    (2006.01)
*G01N 33/574*   (2006.01)
*A61K 39/00*    (2006.01)

(52) U.S. Cl.
CPC ...... *G01N 33/57419* (2013.01); *C07K 14/4748* (2013.01); *G01N 33/57438* (2013.01); *A61K 39/00* (2013.01)

(58) Field of Classification Search
CPC ...... C07K 7/06; C07K 14/4748; A61K 38/04; A61K 38/08; A61K 39/0011
See application file for complete search history.

(56) References Cited

U.S. PATENT DOCUMENTS

| | | | |
|---|---|---|---|
| 6,043,084 A | 3/2000 | Scanlan et al. | |
| 6,218,521 B1 | 4/2001 | Obata | |
| 6,403,373 B1 | 6/2002 | Scanlan et al. | 435/325 |
| 6,517,837 B1 | 2/2003 | Scanlan et al. | |
| 6,607,879 B1 | 8/2003 | Cocks et al. | 435/6 |
| 6,686,147 B1 | 2/2004 | Scanlan et al. | |
| 6,727,066 B2 | 4/2004 | Kaser | 435/6 |
| 6,974,667 B2 | 12/2005 | Horne et al. | 435/6 |
| 6,982,316 B1 | 1/2006 | Scanlan et al. | |
| 7,166,573 B1 * | 1/2007 | Obata | 514/12 |
| 7,378,096 B2 * | 5/2008 | Subjeck et al. | 424/184.1 |
| 2002/0037541 A1 | 3/2002 | Obata | |
| 2006/0251666 A1 | 11/2006 | Nakatsura et al. | 424/185.1 |
| 2008/0044818 A1 | 2/2008 | Nishimura et al. | 435/6 |
| 2009/0074800 A1 | 3/2009 | Nakatsura et al. | |

FOREIGN PATENT DOCUMENTS

| | | |
|---|---|---|
| JP | 2001-504702 | 4/2001 |
| JP | 2001-516009 | 9/2001 |
| JP | 2005-525810 | 9/2005 |
| WO | 98/23735 | 6/1998 |
| WO | WO 99/04265 A2 | 1/1999 |
| WO | 99/16903 | 4/1999 |
| WO | 03/097879 | 11/2003 |
| WO | 2004/020624 | 3/2004 |
| WO | 2007/018198 | 2/2007 |

OTHER PUBLICATIONS

Bowie et al, Science, 247: 1306-1310, 1990.*
Burgess et al, J. Cell Biology, 111 : 2129-2138, 1990.*
Lazar et al, Molecular and Cellular Biology, 8: 1247-1252, 1988.*
Chamberlain, R.S., et al., Expert Opinion on Pharmacotherapy, 1(4): 603-614, 2000.*
Sawada, Y., et al., Oncology Reports, 31: 1051-1058, 2014.*
Toes, R.E.M., et al., Proc. Natl. Acad. Sci. USA, 93: 7855-7860, 1996.*
Stevenovic, S., Nature Reviews, 2: 1-7, 2002.*
Marincola., F.M, et al, TRENDS in Immunology, 24(6): 334-341, 2003.*
Nakatsura, T. et al., "Gene cloning of immunogenic antigens overexpressed in pancreatic cancer," *Biochemical and Biophysical Research Communications*, Academic Press Inc., vol. 281, No. 4, pp. 936-944 (2001).
Kai, M. et al., "Heat shock protein 105 is overexpressed in a variety of human tumors," *Oncology Reports*, vol. 10, No. 6, pp. 1777-1782 (2003).
Takahashi et al., *Nature*, vol. 344, pp. 873-874 (1990).
Bolognesi, *Nature*, vol. 344, pp. 818-819 (1990).
Mouritsen et al., *J. Immunol.*, vol. 148, pp. 1438-1444 (1992).
Kohler et al., *Nature*, vol. 256, pp. 495-497 (1975).
Sahin et al., *Proc. Natl. Acad. Sci. USA* 92:11810-11813 (1995).
Gure et al., *Int. J. Cancer* 72:965-971 (1997).
Güre et al., *Cancer Research* 58:1034-1041 (1998).
Scanlan et al., *Int. J. Cancer* 76:652-658 (1998).
Itoh et al., *International Journal of Oncology* 14:703-708 (1999).
Türeci et al., *Cancer Research* 56: 4766-4772 (1996).

(Continued)

*Primary Examiner* — Alana Harris Dent
*Assistant Examiner* — Anne Holleran
(74) *Attorney, Agent, or Firm* — Greenblum & Bernstein, P.L.C.

(57) ABSTRACT

An object of the present invention to provide: a human pancreatic cancer antigen and/or a human colon cancer antigen that can be applied to the diagnosis and/or treatment of various types of cancers or tumors including pancreatic cancer and colon cancer as representative examples; a gene encoding the same; an anti-cancer vaccine using the same; or the like. The present invention provides a cancer antigen comprising a protein having the amino acid sequence shown in SEQ ID NO: 1; a peptide comprising a portion of said protein and having immune-stimulating activity; an anti-cancer vaccine comprising said peptide; a DNA having the nucleotide sequence shown in SEQ ID NO: 2, or its complementary sequence or a part or full length of these sequence; an anti-cancer vaccine comprising said DNA; and use thereof.

3 Claims, 8 Drawing Sheets

(56) References Cited

OTHER PUBLICATIONS

Brass et al., *Human Molecular Genetics* 6(1):33-39 (1997).
Accession No. AAX40073, Jul. 12, 1999, WO 99/04265-A2, Database N_Geneseq_200701.
Ishihara, K. et al. Biochem. Biophys. Acta, 1444: 138-142, 1999.
U.S. Appl. No. 12/063,165 to Nishimura et al., entitled "Glypican-3 Derived Tumor Rejection Antigenic Peptides Useful for HLA-A2-Positive Patients and Pharmaceutical Comprising the Same."
U.S. Appl. No. 11/577,435 to Nishimura et al., entitled "Novel Diagnostic Kit for Malignant Melanoma."
Singh-Jasuja et al., "The Role of Heat Shock Proteins and Their Receptors in the Activation of the Immune System" *Biol. Chem.* vol. 382, pp. 629-636, 2001.
Ishii et al., "Analysis of Relationship Between Tumor-Derived Heat Shock Protein and Tumor Rejection Antigen" *Immunological allergic*, 15 [2], pp. 128-129, 1997.
*Annual Review Meneki 2002*, p. 244-250, Dec. 5, 2001.
"Heat Shock Protein" *Emergency Concentrated Therapy* vol. 14, No. 9, pp. 969-974, 2002.
The 61$^{st}$ Japanese Cancer Association Annual Meeting, Abstract 1510, p. 177, Aug. 25, 2002.
Minohara et al., "Investigation of a Novel Autoantigen in Opticospinal Form of Multiple Sclerosis" *Neuroimmunology* vol. 10, No. 1, pp. 42-43, 2002.
Japanese Official Action dated Jun. 9, 2009, issued in connection with JP 2004-532775, along with a partial English language translation thereof.
Japanese Official Action dated Oct. 20, 2009, issued in connection with JP 2004-532775, along with a partial English language translation thereof.
Japanese Office Action issued with respect to Japanese Patent App. No. 2010-009018, Jul. 10, 2012.
English language excerpt from "Heat Shock Protein" *Emergency Concentrated Therapy* vol. 14, No. 9, pp. 969-974, 2002.

\* cited by examiner

CANCER ANTIGEN AND USE THEREOF

This application is a divisional of U.S. patent application Ser. No. 10/525,831 filed on Oct. 17, 2005 now abandoned, which is the National Stage of PCT/JP2003/011049, filed Aug. 29, 2003, the entire contents of which are incorporated herein by reference.

TECHNICAL FIELD

The present invention relates to a novel human cancer antigen that is useful for diagnosis of various types of cancers such as pancreatic cancer or colon cancer and for immunotherapy, and use thereof.

BACKGROUND ART

At present, cancer is the number one cause of death. Occurrence mechanisms, diagnostic methods, and therapeutic methods for cancer have been developed. However, a large number of advanced cancers have not yet been treated under the present circumstances. In order to improve the current situation, it is considered to be necessary to develop a novel early diagnostic method and therapeutic method.

Immunotherapy has long been anticipated as a method for treating cancers, and various attempts have been made regarding such therapy. However, sufficient antitumor effects have not yet been exhibited. Conventionally, immunotherapy for cancers had previously been centered on nonspecific immunotherapy. In recent years, however, it has been clarified that T cells play an important role in tumor rejection in living bodies. As a result, efforts are now focused on the isolation of a T cell-recognizing cancer antigen that is capable of inducing cytotoxic T lymphocytes (CTL) and the determination of an MHC class I-binding epitope.

To date, many cancer antigens have been isolated by the conventional cDNA expression cloning method, using CTL. This method requires the establishment of a cell line from tumor and the establishment of CTL. Thus, it is difficult to isolate a tumor antigen from carcinomas other than melanomas. In addition, in order to enhance the effects of immunotherapy, it is considered that a treatment method involving mixing many peptides is effective. In order to establish such a treatment method, it is necessary to isolate a large number of antigens. Thus, the conventional cDNA expression cloning method is problematic in that it takes enormous manpower and time to isolate even a single antigen.

In 1995, Pfreundschuh et al. in Germany and Old et al. in U.S.A. have reported the SEREX method, which detects a cancer antigen protein recognized by an antibody in the serum of a cancer patient (Serological Identification of Recombinant cDNA Expression Cloning; Proc. Natl. Acad. Sci. USA 92, 11810-11813, 1995). Many tumor antigens have been isolated by this method. Among antigens isolated by this method, antigens such as MAGE-1 or tyrosinase that induce CTL have also been included. Accordingly, it is pointed out that this method is also useful as a method for detecting an antigen recognized by cell-mediated immunity. Moreover, it has been reported that a cancer antigen recognized by the IgG antibody of a patient was isolated by the above-described method (Int. J. Cancer 72, 965-971, 1997; Cancer Res. 58, 1034-1041, 1998; Int. J. Cancer 29, 652-658, 1998; Int. J. Oncol. 14, 703-708, 1999; Cancer Res. 56, 4766-4772, 1996; and Hum. Mol. Genet. 6, 33-39, 1997).

DISCLOSURE OF THE INVENTION

It is an object of the present invention to provide: a human pancreatic cancer antigen and/or a human colon cancer antigen that can be applied to the diagnosis and/or treatment of various types of cancers or tumors including pancreatic cancer and colon cancer as representative examples; a gene encoding the same; and an anti-cancer vaccine using the same.

That is to say, the present invention provides a cancer antigen comprising a protein of any of the following (A) or (B):

(A) a protein having the amino acid sequence shown in SEQ ID NO: 1; or (B) a protein having an amino acid sequence comprising a substitution, deletion, insertion, and/or addition of one or several amino acids with respect to the amino acid sequence shown in SEQ ID NO: 1, and also having immune-stimulating activity.

In another aspect, the present invention provides an immune-stimulating agent used for cancers, which comprises the aforementioned cancer antigen of the present invention.

In another aspect, the present invention provides a peptide comprising a portion of the aforementioned cancer antigen of the present invention and having immune-stimulating activity. The peptide of the present invention can preferably activate cytotoxic T lymphocytes recognizing a cancer antigen protein. The peptide of the present invention preferably has the amino acid sequence shown in any one of SEQ ID NOS: 3 to 22.

In another aspect, the present invention provides a peptide, which has an amino acid sequence comprising a substitution, deletion, insertion, and/or addition of one or several amino acids with respect to the amino acid sequence shown in any one of SEQ ID NOS: 3 to 22, and also has immune-stimulating activity. The above-described peptide can preferably activate cytotoxic T lymphocytes which recognize a cancer antigen protein.

In another aspect, the present invention provides an immune-stimulating agent used for cancers, which comprises any one of the above-described peptides.

In another aspect, the present invention provides DNA encoding the aforementioned cancer antigen of the present invention.

In another aspect, the present invention provides DNA of any one of the following (a), (b), and (c):

(a) DNA having the nucleotide sequence shown in SEQ ID NO: 2;

(b) DNA hybridizing with the DNA having the nucleotide sequence shown in SEQ ID NO: 2 under stringent conditions, and encoding a protein having immune-stimulating activity; and (c) DNA having a partial sequence of the DNA of (a) or (b) above, and encoding a protein having immune-stimulating activity.

In another aspect, the present invention provides an antibody against the aforementioned cancer antigen or peptide of the present invention.

In another aspect, the present invention provides helper T cells, cytotoxic T lymphocytes, or an immunocyte population comprising these cells, which are induced by in vitro stimulation using the aforementioned cancer antigen or peptide of the present invention, or a mixture thereof.

In another aspect, the present invention provides helper T cells, cytotoxic T lymphocytes, or an immunocyte population comprising these cells, which are induced by in vitro stimulation using the aforementioned cancer antigen or peptide of the present invention, or a mixture thereof, and an immune activator. The immune activator is preferably a cell growth factor or cytokine.

In another aspect, the present invention provides a method for suppressing a tumor, which comprises introducing the above-described helper T cells, cytotoxic T lymphocytes, or an immunocyte population comprising these cells into a body. The above-described method is preferably used to prevent and/or treat cancers.

In another aspect, the present invention provides a cell culture solution used to produce the helper T cells or cytotoxic T lymphocytes of the present invention or an immunocyte population comprising these cells, which comprises the aforementioned cancer antigen or peptide of the present invention, or a mixture thereof.

In another aspect, the present invention provides a cell culture kit for producing the helper T cells or cytotoxic T lymphocytes of the present invention or an immunocyte population comprising these cells, which comprises the above-described cell culture solution and a cell culture vessel.

In another aspect, the present invention provides a cancer vaccine comprising the aforementioned cancer antigen and/or at least one type of peptide of the present invention. The above-described cancer vaccine preferably further comprises an adjuvant.

In another aspect, the present invention provides a cancer vaccine, which comprises the aforementioned DNA of the present invention, or recombinant virus or recombinant bacteria comprising the above-described DNA. The above-described cancer vaccine preferably further comprises an adjuvant.

In another aspect, the present invention provides a probe for diagnosing cancers, which comprises the aforementioned DNA of the present invention.

In another aspect, the present invention provides an agent for diagnosing cancers, which comprises the aforementioned cancer diagnostic probe and/or antibody of the present invention.

In another aspect, the present invention provides an agent for preventing and/or treating cancers, which comprises the aforementioned cancer antigen, peptide, antibody, and/or helper T cells, cytotoxic T lymphocytes, or an immunocyte population comprising these cells of the present invention.

In the present invention, cancer is preferably pancreatic cancer, colon cancer, brain tumor, malignant melanoma, chronic myelocytic leukemia, acute myelocytic leukemia, lymphoma, esophageal cancer, kidney cancer, prostatic cancer, lung cancer, breast cancer, stomach cancer, hepatic cancer, gallbladder cancer, testicular cancer, uterine cancer, ovarian cancer, thyroid cancer, bladder cancer, or sarcoma.

BEST MODE FOR CARRYING OUT THE INVENTION

Figure 1:
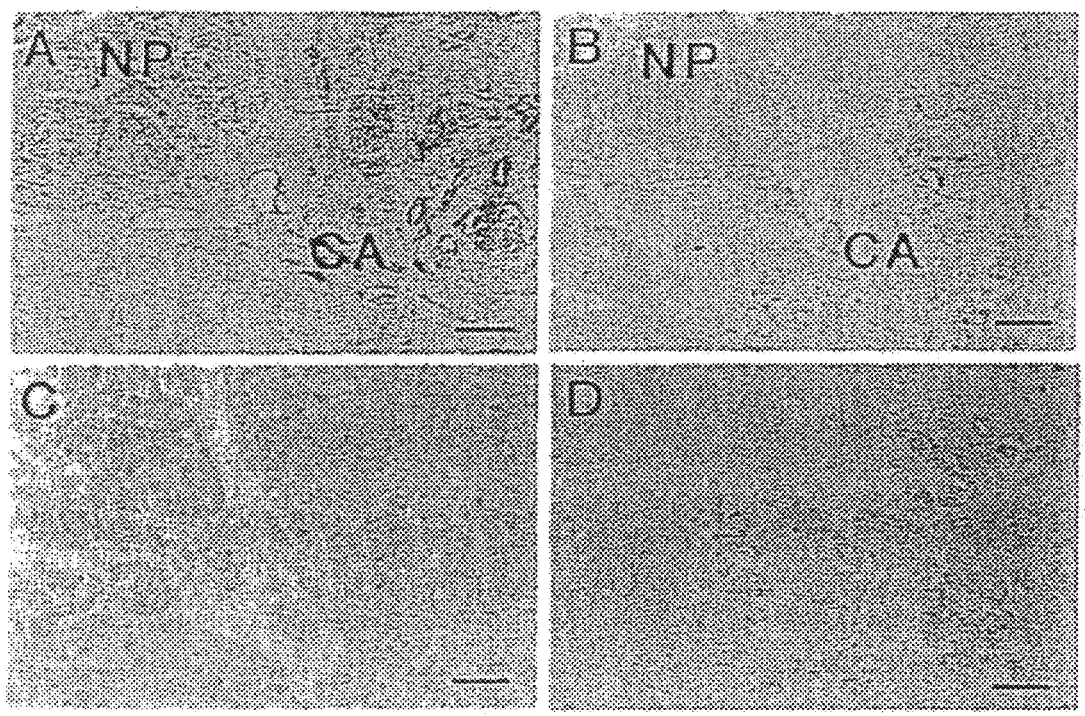
FIG. 1 is a microphotograph showing the results of an immunohistochemical analysis on hsp105 in pancreatic cancer. In the figure, the symbols have the following meanings:
A: a pancreatic cancer portion and a peripheral non-cancerous portion stained with hematoxylin and eosin, CA: a cancerous portion, NP: a non-cancerous portion
B: An hsp105 protein is highly expressed in cancer cells. It is weakly expressed also in a non-cancerous portion.
C: A non-cancerous portion is significantly expanded. An hsp105 protein is weakly expressed in the cytoplasm.
D: A cancerous portion is significantly expanded. An hsp105 protein is highly expressed mainly in the cytoplasm of cancer cells.

The embodiments of the present invention will be described in detail below.
(1) The Cancer Antigen, Peptide, and Immune-Stimulating Agent Against Cancers According to the Present Invention The cancer antigen of the present invention collected from pancreatic cancer or colon cancer is a protein of any of the following (A) or (B):
(A) a protein having the amino acid sequence shown in SEQ ID NO: 1 (hereinafter referred to as "hsp105"); or
(B) a protein having an amino acid sequence comprising a substitution, deletion, insertion, and/or addition of one or several amino acids with respect to the amino acid sequence shown in SEQ ID NO: 1, and also having immune-stimulating activity.

The term "protein having immune-stimulating activity" is used in the present specification to mean a protein having activity of inducing an immune response such as generation of an antibody or cell-mediated immunity. Among them, a protein having T cell-stimulating activity of stimulating cytotoxic T lymphocytes (killer T cells/CTL) is particularly preferable.

hsp105 is a heat shock protein with a high molecular weight, which belongs to the hsp110/105 family, and is composed of hsp105α and 105β. 105α is a heat shock protein of 105 kDa, and is induced by various stresses. 105β is a protein generated by splicing of mRNA of 105α, and has a molecular weight smaller than that of 105α. hsp105 that is an antigen of pancreatic cancer or colon cancer of the present invention can be detected, for example, by the SEREX method as described later in examples in the present specification.

In the present invention, the scope of "one or several" in "an amino acid sequence comprising a substitution, deletion, insertion, and/or addition of one or several amino acids with respect to the amino acid sequence shown in SEQ ID NO: 1" is not particularly limited. For example, it means 1 to 20, preferably 1 to 10, more preferably 1 to 7, further preferably 1 to 5, and particularly preferably 1 to 3 amino acids.

A method of obtaining or producing the cancer antigen protein of the present invention is not particularly limited. A naturally occurring protein, a chemically synthesized protein, or a recombinant protein produced by genetic engineering may be used. From the viewpoint that it can be produced in large volume by relatively easy operations, a recombinant protein is preferable.

When a naturally occurring protein is obtained, it can be isolated from cells or tissues expressing the protein by appropriate combined use of protein isolation and purification methods. When a chemically synthesized protein is obtained, the protein of the present invention can be synthesized by chemical synthesis methods such as the Fmoc method (fluorenylmethyloxycarbonyl method) or the tBoc method (t-butyloxycarbonyl method). Moreover, the protein of the present invention can also be synthesized by using various types of commercially available peptide synthesizers.

When the cancer antigen protein of the present invention is produced in the form of a recombinant protein, it can be produced by obtaining DNA having a nucleotide sequence encoding the protein (e.g. the nucleotide sequence shown in SEQ ID NO: 2), a mutant thereof, or a homologue thereof, and introducing it into a preferred expression system.

Any expression vector can be used, as long as it can autonomously replicate in host cells or it can be incorporated into the chromosomes of host cells. An expression vector containing a promoter at a site that is capable of expressing the gene of the present invention, is used. A transformant having a gene encoding the protein of the present invention can be produced by introducing the aforementioned expression vector into a host. Such a host used herein may include bacteria, yeast, animal cells, and insect cells. In addition, an expression vector may be introduced into a host by known methods, depending on the type of the host.

In the present invention, the transformant having the gene of the present invention produced as described above is cultured, and the protein of the present invention is generated and accumulated in a culture product. Thereafter, the protein of the present invention is collected from the culture product, thereby isolating a recombinant protein.

When the transformant of the present invention is prokaryote such as *Escherichia coli* or eukaryote such as yeast, either a natural medium or a synthetic medium may be used as a medium in which these microorganisms are cultured, as long as it contains a carbon source, a nitrogen source, and inorganic salts that can be assimilated by the microorganisms, and the culture of the transformant can efficiently be carried out therein. In addition, culture may be carried out under conditions that are commonly used for culturing microorganisms. After completion of the culture, the protein of the present invention may be isolated and purified from the culture product of the transformant by common protein isolation and purification methods.

A protein having an amino acid sequence comprising a substitution, deletion, insertion, and/or addition of one or several amino acids with respect to the amino acid sequence shown in SEQ ID NO: 1, can appropriately be produced or obtained by persons skilled in the art on the basis of the information regarding the nucleotide sequence shown in SEQ ID NO: 2, which is an example of the DNA sequence encoding the amino acid sequence shown in SEQ ID NO: 1.

That is to say, a gene (mutant gene) having a nucleotide sequence encoding a protein having an amino acid sequence comprising a substitution, deletion, insertion, and/or addition of one or several amino acids with respect to the amino acid sequence shown in SEQ ID NO: 1, can be produced by any given methods that are known to persons skilled in the art, such as chemical synthesis, genetic engineering methods, or mutagenesis. Specifically, a mutation is introduced into DNA having the nucleotide sequence shown in SEQ ID NO: 2, so as to obtain mutant DNA.

For example, a method of allowing DNA to come into contact with an agent acting as a mutagen, a method of irradiating with ultraviolet rays, a genetic engineering method, and the like, can be applied to the DNA having the nucleotide sequence shown in SEQ ID NO: 2. Site-directed mutagenesis, one of the genetic engineering methods, is useful because it is capable of introducing a specific mutation into a specific site. Site-directed mutagenesis can be carried out according to the methods described in publications such as Molecular Cloning: A laboratory Manual, 2$^{nd}$ Ed., Cold Spring Harbor Laboratory, Cold Spring Harbor, N.Y., 1989 (hereinafter abbreviated as Molecular Cloning 2$^{nd}$ Ed.); and Current Protocols in Molecular Biology, Supplements 1 to 38, John Wiley & Sons (1987-1997) (hereinafter abbreviated as Current Protocols in Molecular Biology).

The present invention also relates to a peptide that is a portion of the aforementioned protein of the present invention and has immune-stimulating activity. The peptide of the present invention preferably can activate cytotoxic T lymphocytes which recognize a cancer antigen protein. Specific examples of such a peptide may include those having any one of the following amino acid sequences:

```
                                            (SEQ ID NO: 3)
    Asn-Tyr-Gly-Ile-Tyr-Lys-Gln-Asp-Leu (SEQ ID NO: 4)
    Ala-Phe-Asn-Lys-Gly-Lys-Leu-Lys-Val-Leu (SEQ ID NO: 5)
    Lys-Tyr-Lys-Leu-Asp-Ala-Lys-Ser-Lys-Ile (SEQ ID NO: 6)
    Gln-Phe-Glu-Glu-Leu-Cys-Ala-Glu-Leu (SEQ ID NO: 7)
    Met-Tyr-Ile-Glu-Thr-Glu-Gly-Lys-Met-Ile (SEQ ID NO: 8)
    Thr-Phe-Leu-Arg-Arg-Gly-Pro-Phe-Glu-Leu (SEQ ID NO: 9)
    Glu-Tyr-Val-Tyr-Glu-Phe-Arg-Asp-Lys-Leu (SEQ ID NO: 10)
    His-Tyr-Ala-Lys-Ile-Ala-Ala-Asp-Phe (SEQ ID NO: 11)
    Lys-Tyr-Asn-His-Ile-Asp-Glu-Ser-Glu-Met (SEQ ID NO: 12)
    Ser-Leu-Asp-Glu-Lys-Pro-Arg-Ile-Val-Val
```

-continued

Arg-Leu-Tyr-Gln-Glu-Cys-Glu-Lys-Leu (SEQ ID NO: 13)

Lys-Leu-Met-Ser-Ser-Asn-Ser-Thr-Asp-Leu (SEQ ID NO: 14)

Leu-Met-Ser-Ser-Asn-Ser-Thr-Asp-Leu (SEQ ID NO: 15)

Ser-Gln-Phe-Glu-Glu-Leu-Cys-Ala-Glu-Leu (SEQ ID NO: 16)

Lys-Ile-Gly-Arg-Phe-Val-Val-Gln-Asn-Val (SEQ ID NO: 17)

Tyr-Val-Tyr-Glu-Phe-Arg-Asp-Lys-Leu (SEQ ID NO: 18)

Leu-Leu-Thr-Glu-Thr-Glu-Asp-Trp-Leu (SEQ ID NO: 19)

Trp-Leu-Tyr-Glu-Glu-Gly-Glu-Asp-Gln-Ala (SEQ ID NO: 20)

Glu-Leu-Met-Lys-Ile-Gly-Thr-Pro-Val (SEQ ID NO: 21)

Val-Met-Asn-Ala-Gln-Ala-Lys-Lys-Ser-Leu (SEQ ID NO: 22)

Moreover, peptides having an amino acid sequence comprising a substitution, deletion, insertion and/or addition of one or several amino acids with respect to the amino acid sequence shown in any one of the above SEQ ID NOS: 3 to 22, and having immune-stimulating activity, are also included in the scope of the present invention. A preferred example of such a peptide may be a peptide capable of activating cytotoxic T lymphocytes which recognize a cancer antigen protein.

In the present invention, the scope of "one or several" in "an amino acid sequence comprising a substitution, deletion, insertion and/or addition of one or several amino acids with respect to the amino acid sequence shown in any one of the above SEQ ID NOS: 3 to 22" is not particularly limited. The number of amino acids is, for example 1 to 5, preferably 1 to 4, more preferably 1 to 3, further preferably 1 or 2, and particularly preferably 1.

The peptide of the present invention can be synthesized by chemical synthesis methods such as the Fmoc method (fluorenylmethyloxycarbonyl method) or the tBoc method (t-butyloxycarbonyl method). Moreover, the peptide of the present invention can also be synthesized using various types of commercially available peptide synthesizers.

The aforementioned cancer antigen protein and peptide of the present invention can induce immunity against cancers, as described later in examples. Accordingly, the present invention provides an immune-stimulating agent against cancers, which comprises the cancer antigen protein or peptide of the present invention.

The immune-stimulating agent against cancers of the present invention is used in vitro or in vivo, and preferably in vitro, so as to induce helper T cells, cytotoxic T lymphocytes, or an immunocyte population containing these cells, thereby providing immunity against cancers.

(2) DNA of the Present Invention

The DNA of the present invention encodes the cancer antigen protein of the present invention described in (1) above. It is preferably DNA of any one of the following (a), (b), and (c):
(a) DNA having the nucleotide sequence shown in SEQ ID NO: 2;
(b) DNA hybridizing with the DNA having the nucleotide sequence shown in SEQ ID NO: 2 under stringent conditions, and encoding a protein having immune-stimulating activity; and
(c) DNA having a partial sequence of the DNA according to (a) or (b) above, and encoding a protein having immune-stimulating activity.

The above term "DNA hybridizing with . . . under stringent conditions" is used to mean the nucleotide sequence of DNA obtained by the colony hybridization method, the plaque hybridization method, or the Southern hybridization method, using DNA as a probe. For example, such DNA can be identified by hybridizing a filter, on which colony- or plaque-derived DNA or a DNA fragment thereof has been immobilized, at 65° C. in the presence of 0.7 to 1.0 M NaCl, and then washing the filter at 65° C. with a 0.1 to 2×SSC solution (wherein 1×SSC solution consists of 150 mM sodium chloride and 15 mM sodium citrate). Hybridization can be carried out by the method described in Molecular Cloning $2^{nd}$ Ed.

DNA having a certain level of homology with the nucleotide sequence of DNA used as a probe is an example of the above DNA hybridizing under stringent conditions. Such DNA has homology of, for example 70% or more, preferably 80% or more, more preferably 90% or more, further preferably 93% or more, particularly preferably 95% or more, and most preferably 98% or more, with the DNA used as a probe.

A method of obtaining the DNA of the present invention is not particularly limited. Suitable probes or primers are prepared based on the information regarding the amino acid sequence and the nucleotide sequence shown in SEQ ID NOS: 1 and 2 in the sequence listing in the present specification, and the cDNA library of a human and the like is screened using such probes or primers, so as to isolate the DNA of the present invention. Such a cDNA library is preferably produced from a cell, organ, or tissue, which expresses the DNA of the present invention.

It is also possible to produce the DNA having the nucleotide sequence shown in SEQ ID NO: 2 by the PCR method. Using human chromosomal DNA or cDNA library as a template, PCR is carried out with a pair of primers that have been designed to amplify the nucleotide sequence shown in SEQ ID NO: 2. PCR reaction conditions can be determined as appropriate. For example, a reaction process consisting of 94° C. and 30 seconds (denaturation), 55° C. and 30 seconds to 1 minute (annealing), and 72° C. and 2 minutes (elongation) is defined as 1 cycle. Such a reaction process is carried out 30 cycles, and thereafter, a reaction consisting of 72° C. and 7 minutes is carried out. Thereafter, the amplified DNA fragment is cloned into a suitable vector capable of replicating in a host such as *Escherichia coli*.

The aforementioned preparation of probes or primers, construction of a cDNA library, screening of a cDNA library, and cloning of a gene of interest are already known to persons skilled in the art. These operations can be carried out according to the methods described in Molecular Cloning $2^{nd}$ Ed., Current Protocols in Molecular Biology, and the like.

(3) Antibody of the Present Invention

The present invention further relates to an antibody recognizing a portion or the entire of the aforementioned protein or peptide of the present invention as an epitope (antigen), and cytotoxic (killer) T lymphocytes (CTL) induced by in vitro stimulation using the above-described protein or peptide. In general, CTL exhibits stronger antitumor activity than an antibody.

The antibody of the present invention may be either a polyclonal antibody or a monoclonal antibody. It can be produced by common methods.

For example, a polyclonal antibody can be obtained by immunizing a mammal with the protein of the present invention as an antigen, collecting the blood from the mammal, and then separating and purifying an antibody from the collected blood. Examples of a mammal to be immunized may include a mouse, a hamster, a Guinea pig, a chicken, a rat, a rabbit, a dog, a goat, a sheep, and a bovine. The immunization method is known to those skilled in the art. For example, an antigen may be administered 2 or 3 times at intervals of 7 to 30 days. The dosage may be set at approximately 0.05 to 2 mg of antigen per administration. An administration route is not particularly limited. A suitable administration route can appropriately be selected from subcutaneous administration, intracutaneous administration, intraperitoneal administration, intravenous administration, and intramuscular administration. In addition, an antigen can be dissolved in a suitable buffer solution containing a commonly used adjuvant such as Freund's complete adjuvant or aluminum hydroxide, before use.

Such an immunized mammal has been bred for a certain period of time, and when its antibody titer begins to increase, a booster can be carried out using 100 μg to 1,000 μg of the antigen, for example. 1 or 2 months after the final administration, the blood is collected from the immunized mammal. The collected blood is then separated and purified by common methods including centrifugation, precipitation using ammonium sulfate or polyethylene glycol, or chromatography such as gel filtration chromatography, ion exchange chromatography, or affinity chromatography, so as to obtain a polyclonal antibody recognizing the protein of the present invention as a polyclonal antiserum.

On the other hand, a monoclonal antibody can be obtained by preparing hybridomas. Hybridomas can be obtained by cell fusion between antibody-generating cells and myeloma cells, for example. Hybridomas which generate the monoclonal antibody of the present invention can be obtained by the following cell fusion method.

Spleen cells, lymph node cells, B lymphocytes or the like collected from the immunized animal are used as antibody-generating cells. The protein of the present invention or a partial peptide thereof is used as an antigen. A mouse, a rat, or the like can be used as an animal to be immunized. The administration of an antigen to such an animal is carried out by common methods. For example, a suspension or emulsified liquid of an adjuvant such as Freund's complete adjuvant or Freund's incomplete adjuvant and the protein of the present invention used as an antigen is administered intravenously, subcutaneously, intracutaneously, or interperitoneally to an animal several times for immunization. For example, spleen cells are obtained from the thus immunized animal as antibody-generating cells, and the obtained cells are fused with myeloma cells by a known method (G. Kohler et al., Nature, 256, 495 (1975)), so as to produce hybridomas.

Examples of a myeloma cell line used for cell fusion may include mouse P3X63Ag8, mouse P3U1 line, and mouse Sp2/0 line. For cell fusion, fusion promoting agents such as polyethylene glycol or Sendai virus are used. For selection of hybridomas after completion of the cell fusion, hypoxanthine aminopterin thymidine (HAT) medium is used according to common methods. Hybridomas obtained by cell fusion are cloned by limiting dilution or the like. Thereafter, as necessary, screening is carried out by enzyme immunoassay using the protein of the present invention, so as to obtain a cell line generating a monoclonal antibody specifically recognizing the protein of the present invention.

In order to produce a monoclonal antibody of interest from the thus obtained hybridoma, the hybridoma may be cultured by the common cell culture method or ascites formation method, and the monoclonal antibody may be purified from the culture supernatant or ascites. The monoclonal antibody can be purified from the culture supernatant or ascites by common methods. For example, ammonium sulfate fractionation, gel filtration, ion exchange chromatography, affinity chromatography, and the like can appropriately be used in combination.

Moreover, fragments of the aforementioned antibody are also included in the scope of the present invention. Examples of such an antibody fragment may include a $F(ab')_2$ fragment and a Fab' fragment.

Furthermore, a labeled antibody obtained by labeling the aforementioned antibody is also included in the scope of the present invention. That is to say, the antibody of the present invention produced as described above can be labeled before use. The type of a substance used to label the antibody of the present invention and a labeling method are known to persons skilled in the art. Examples of such a labeling method may include: enzyme labeling with horseradish peroxidase or alkaline phosphatase; fluorescent labeling with FITC (fluorescein isothiocyanate) or TRITC (tetramethylrhodamine B isothiocyanate); labeling with color substances such as colloidal metal or colored latex; affinity labeling with biotin; and isotopic labeling with $^{125}$I. The analysis or measurement of the protein of the present invention (that is a cancer antigen) with the labeled antibody of the present invention can be carried out according to methods widely known to those skilled in the art, such as the enzyme antibody technique, immunohistological staining, immunoblotting, the direct fluorescent antibody method, or the indirect fluorescent antibody method.

(4) Helper T Cells, Cytotoxic T Lymphocytes, or Immunocyte Population Containing these Cells The present invention further relates to helper T cells, cytotoxic T lymphocytes, or an immunocyte population containing these cells, which are induced by in vitro stimulation using the cancer antigen or peptide of the present invention or a mixture thereof. For example, when peripheral blood lymphocytes or tumor-infiltrating lymphocytes are stimulated in vitro with the protein or peptide of the present invention, tumor responsive activated T cells are induced. The activated T cells can effectively be used for adoptive immunotherapy. Moreover, the cancer antigen or peptide of the present invention is allowed to express in dendritic cells that are strong antigen presenting cells in vivo or in vitro, thereby conducting immune stimulation by administration of the dendritic cells wherein the antigen has been expressed.

Preferably, helper T cells, cytotoxic T lymphocytes, or an immunocyte population containing these cells are induced by in vitro stimulation using the cancer antigen or peptide of the present invention or a mixture thereof and an immune activator. Examples of an immune activator used herein may include a cell growth factor and cytokine.

The helper T cells, cytotoxic T lymphocytes, or an immunocyte population containing these cells obtained as described above are transferred into a body to suppress tumor, thereby preventing and/or treating cancers.

Moreover, helper T cells, cytotoxic T lymphocytes, or an immunocyte population containing these cells, which can suppress tumor as described above, can be produced using the cancer antigen or peptide of the present invention or a mixture thereof. Accordingly, the present invention provides a cell culture solution containing the cancer antigen or peptide of the present invention or a mixture thereof. Using such a cell culture solution, the helper T cells, cytotoxic T lymphocytes, or an immunocyte population containing these cells, which can suppress tumor, can be produced. Further, the present invention provides a cell culture kit for producing the helper T cells, cytotoxic T lymphocytes, or an immunocyte population containing these cells, which comprises the aforementioned cell culture solution and a cell culture vessel.

(5) Cancer Vaccine of the Present Invention

Since the DNA, cancer antigen, and peptide of the present invention can induce cancer cell-specific cytotoxic T lymphocytes, they are anticipated as therapeutic and/or preventive agents used for cancers. For example, BCG bacteria transformed by recombinant DNA obtained by incorporating the DNA of the present invention into a suitable vector, or viruses such as vaccinia virus into the genome of which the DNA of the present invention has been incorporated, can effectively be used as live vaccine for treating and/or preventing human cancers. The dosage and administration method of such a cancer vaccine are the same as those of ordinary vaccination or BCG vaccine.

Namely, the DNA of the present invention (as is, or in the form of plasmid DNA that is incorporated into an expression vector), and recombinant virus or recombinant bacteria containing the above DNA are administered as a cancer vaccine to mammals including a human, directly or in a state where they are dispersed in an adjuvant. Also, the peptide of the present invention can be administered thereto as a cancer vaccine, in a state where it is dispersed in an adjuvant.

Examples of an adjuvant used in the present invention may include Freund's incomplete adjuvant, BCG, trehalose dimycolate (TDM), lipopolysaccharide (LPS), alum adjuvant, and silica adjuvant. From the viewpoint of ability to induce antibody, Freund's incomplete adjuvant (FIA) is preferably used.

(6) Probe for Diagnosing Cancers, Agent for Diagnosing Cancers, and Preventive and/or Therapeutic Agent Against Cancers According to the Present Invention The DNA of the present invention can be used as a diagnostic probe, in which DNAs of various types of human cancers are extracted and the homology between them is examined. Moreover, this probe and the above-described antibody can also be used as an agent for diagnosing cancers.

That is to say, the present invention relates to a probe for diagnosing cancers, which comprises an entire or a part of the antisense strand of DNA or RNA encoding the protein of the present invention. The present invention also relates to an agent for diagnosing cancers, which comprises the above-described probe for diagnosing cancers or an antibody reacting with the protein of the present invention. The probe for diagnosing cancers of the present invention is preferably the entire or a part of the antisense strand of DNA (cDNA) or RNA (cRNA) encoding the protein of the present invention, which preferably has a length that is long enough as a probe (at least 20 bases). For example, mRNA of the protein (cancer antigen) of the present invention obtained from an analyte is detected using the above-described antisense strand, thereby enabling the diagnosis of cancers. Examples of an analyte used for detection may include genomic DNA that can be obtained by biopsy of the cells of a subject, such as the blood, urine, saliva, or tissues; RNA; and cDNA, but examples are not limited thereto. When such an analyte is used, those amplified by PCR and the like may also be used.

The type of cancer is not particularly limited in the present specification. Specific examples of cancer may include pancreatic cancer, colon cancer, brain tumor, malignant melanoma, chronic myelocytic leukemia, acute myelocytic leukemia, lymphoma, esophageal cancer, kidney cancer, prostatic cancer, lung cancer, breast cancer, stomach cancer, hepatic cancer, gallbladder cancer, testicular cancer, uterine cancer, ovarian cancer, thyroid cancer, bladder cancer, and sarcoma.

The immune response of a cancer patient to cancer cells is unexpectedly active, and it is found that IgG antibodies are generated to various types of proteins. As described later in examples, hsp105 that is the antigen protein of the present invention is highly expressed specifically in pancreatic cancer, colon cancer, breast cancer, esophageal cancer, malignant lymphoma, pheochromocytoma, thyroid cancer, bladder cancer, and seminoma.

The protein or peptide of the present invention can induce cancer cell-specific cytotoxic T lymphocytes as T cell epitopes. Thus, it is useful as a preventive and/or therapeutic agent used for human cancers. In addition, the antibody of the present invention is also effective as a preventive and/or therapeutic agent used for human cancers, as long as it can inhibit the activity of the protein of the present invention that is a cancer antigen. As a practical usage, the protein, peptide, or antibody of the present invention may be administered directly, or together with a pharmaceutically acceptable carrier and/or diluent, or also together with the below-mentioned assistant agents, as necessary, so as to create an injection. Otherwise, it may also be administered by percutaneous absorption via the mucosa according to a method such as spraying. The term "carrier" is used herein to mean, for example, human serum albumin. Examples of a diluent may include PBS and distilled water.

As a dosage, the cancer antigen, peptide, or antibody of the present invention may be administered within a range between 0.01 mg and 100 mg per once per adult. However, a dosage is not limited to the above range. Also, the dosage form is not particularly limited. A freeze-dried product, or granules produced by adding an excipient such as sugar to the cancer antigen, peptide, or antibody of the present invention, may also be used.

Examples of an assistant agent that can be added to the agent of the present invention to enhance the activity of inducing cytotoxic T lymphocytes may include fungal components of BCG bacteria or the like, ISCOM described in Nature, vol. 344, p. 873 (1990), QS-21 of saponins described in J. Immunol. vol. 148, p. 1438 (1992), liposome, and aluminum hydroxide. In addition, immune activators such as lenthinan, schizophyllan, or Picibanil may also be used as assistant agents. Moreover, cytokines which promote the growth or differentiation of T cells, such as IL-2, IL-4, IL-12, IL-1, IL-6, or TNF, may also be used as assistant agents.

Furthermore, the above-described antigen peptide is added to cells collected from a patient or cells having the same HLA haplotype in a test tube, so as to allow the cells to present an antigen. Thereafter, it is administered into the blood vessel of the patient, so that cytotoxic T lymphocytes can effectively be induced in the patient body. Moreover, the above-described peptide is added to the peripheral blood lymphocytes of a patient, and it is then cultured in a test tube, so that cytotoxic T lymphocytes can be induced in the test tube and then returned to the blood vessel of the patient. Such a treatment involving cell transfer has already been conducted as a cancer treatment, and thus, it has been well known to persons skilled in the art.

A target antigen in the specific antitumor immunotherapy is required to be an antigen recognized by cytotoxic T lymphocytes (killer T cells/CTL). The antigen of the present invention has increased in vitro killer T cell-stimulating activity on HLA-A24 that is widely found in Japanese, or on HLA-A2 that is widely found over the world. Thus, the injection of the antigen of the present invention into a body induces the activation of CTL, and as a result, it can be anticipated that antitumor effects be obtained. Moreover, when lymphocytes are stimulated with the antigen of the present invention in vitro, activated T cells are induced. The thus activated T cells are injected into an affected area. Thus, this method can effectively be used as an adoptive immunotherapy.

EXAMPLES

The antigen of the present invention, the production method thereof, and the effects thereof will be described in the following examples. However, these examples are not intended to limit the scope of the present invention.

Example 1

Collection of Serum

The serum was collected from a patient with pancreatic cancer. The collected serum was conserved at −80° C. From this serum sample, an antibody reacting with *Escherichia coli* and λ phage was eliminated by using a column that was filled with dissolved matter of *Escherichia coli* and phage and sepharose 4B. Thereafter, the resultant serum was 100 to 800 times diluted and then used.

<cDNA Library and Production of Protein>

A phage cDNA library produced by inserting cDNA of a pancreatic cancer cell line CFPAC-1 into a λZAP express vector was purchased from Stratagene, La Jolla, Calif. *Escherichia coli* was infected with this λ phage cDNA library, and it was then cultured on NZY plate medium at 42° C. for 6 hours, so as to produce plaques. Thereafter, the plate was covered with a nitrocellulose membrane into which isopropyl β-D-thiogalactoside (IPTG) had been infiltrated at 37° C. for 3 hours, so as to produce a protein encoded by the cDNA that had been incorporated into λ phage in the plaques.

<Immunoscreening>

The protein produced by the aforementioned method was transferred into a nitrocellulose membrane. After blocking, the nitrocellulose was washed, and it was then allowed to react with the above-described serum at 4° C. for 15 hours. After washing, a horseradish peroxidase (HRP)-labeled mouse anti-human IgG antibody was used as a secondary antibody, and it was allowed to react with the membrane. After washing, chemoluminescence was detected on an X-ray film, and it was compared with the plate on a photograph, so that positive plaques were picked up together with the peripheral negative plaques. Plaques corresponding to positive sites in a color reaction were collected from a 15-cm NZY agarose plate. The collected plaques were then dissolved in an SM buffer solution (100 mM NaCl, 10 mM $MgSO_4$, 50 mM Tris-HCl, and 0.01% gelatin; pH 7.5). The color reaction positive plaques were subjected to a second screening and a third screening by the same above method, until they became a single colony, thereby obtaining a single phage clone with which an IgG antibody in the serum reacts. By the above-described method, 63 positive clones were isolated from cDNA derived from the pancreatic cancer cell line.

<Homology Search of Isolated Antigen Gene>

Insert DNA was amplified by the PCR method, and it was used for the subsequent analysis. The obtained PCR product was sequenced using Big Dye DNA sequencing kit (PE Biosystems, CA), so as to determine a nucleotide sequence thereof. Using homology search program BLAST (Basic Local Alignment Search Tool), each of the thus determined nucleotide sequences of 63 types of genes was compared with the gene information registered in the NCBI databank.

<hsp105>

As a result, 18 positive clones shown in Table 1 were found. One of the positive clones was hsp105.

TABLE 1

Genes Isolated by SEREX of a Pancreatic Ductal Adenocarcinoma Cell Line

| Gene designation | Gene/sequence identity | SEREX database search[a] |
|---|---|---|
| KM-PA-1 | apg-2 (heat shock protein 110 family) | NGO-St-81, NY-CO-40, NY-CO-32 |
| KM-PA-2 | EST (KIAA0124) | — |
| KM-PA-3 | β-actin | — |
| KM-PA-4 | coactosin-like protein (CLP) | — |
| KM-PA-5 | HALPHA44 (alpha-tubulin) | — |
| KM-PA-6 | unknown | — |
| KM-PA-7 | CDC-like kinase (CLK3) | — |
| KM-PA-8 | cytokeratin 18 | — |
| KM-PA-9 | polyA binding protein | — |
| KM-PA-10 | very-long-chain-acyl-CoA-dehydrogenase (VLCAD) | — |
| KM-PA-11 | unknown | — |
| KM-PA-12 | HLA-Cw heavy chain (MHC Class I) | LONY-BR-26 |
| KM-PA-13 | unknown | — |
| KM-PA-14 | CGI 55 protein | — |
| KM-PA-15 | glycosylation-inhibiting factor (GIF) | Mz19-16a, Hom-HD1-21 |
| KM-PA-16 | unknown | NGO-St-95, NGO-St-103 |
| KM-PA-17 | DNA binding protein A (dbpA) | — |
| KM-PA-18 | heat shock protein 105 (KIAA0201) | NY-CO-25 |

[a]Dash means no strong homology.

<Confirmation of Expression of hsp105>

Figure 2:
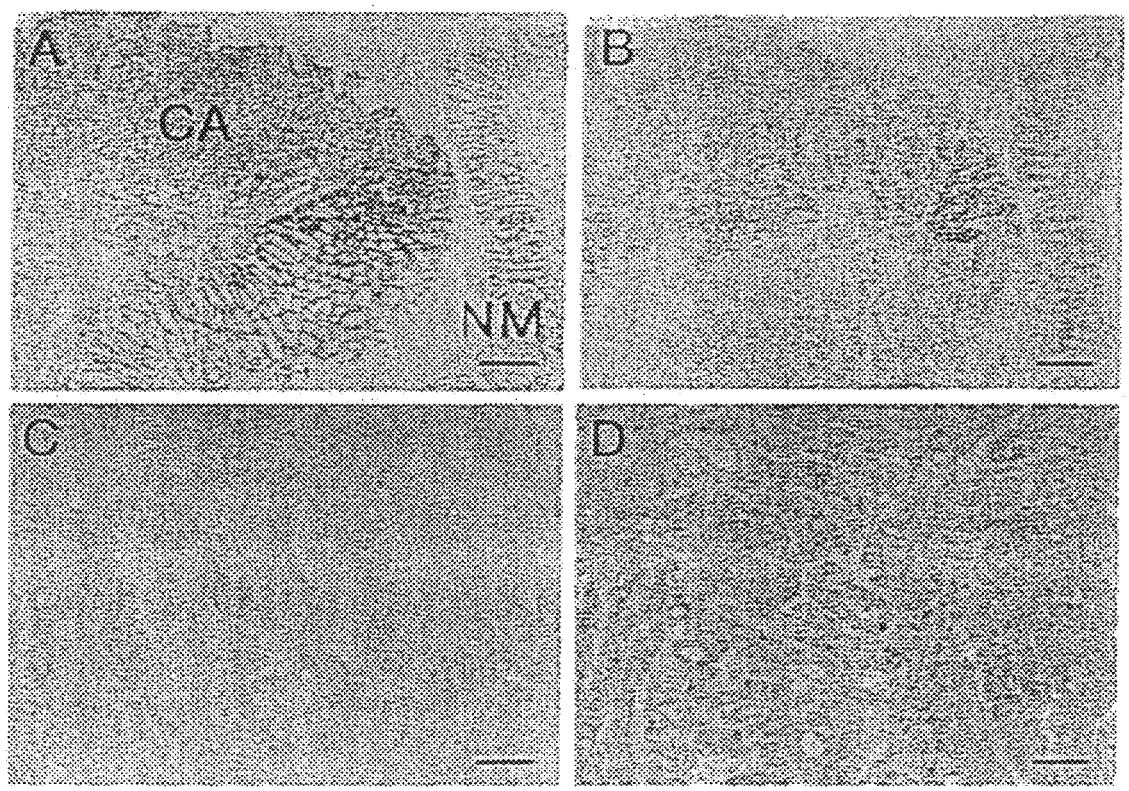
FIG. 2 is a microphotograph showing the results of an immunohistochemical analysis on hsp105 in colon cancer. In the figure, the symbols have the following meanings:
A: a colon cancer portion and a peripheral non-cancerous portion stained with hematoxylin and eosin, CA: a cancerous portion, NP: a non-cancerous portion
B: An hsp105 protein is highly expressed in cancer cells. It is weakly expressed also in a non-cancerous portion.
C: A non-cancerous portion is significantly expanded. An hsp105 protein is weakly expressed in the cytoplasm.
D: A cancerous portion is significantly expanded. An hsp105 protein is highly expressed mainly in the cytoplasm of cancer cells. Also, the hsp105 protein is weakly expressed in the nucleus thereof.

The presence or absence of the expression of an hsp105 protein was immunohistochemically analyzed in various types of cancer tissues and in normal tissues. As a result, it was found that hsp105 is expressed in pancreatic cancer tissues and in colon cancer tissues, as shown in FIGS. 1 and 2.

Example 2

Peptide Constituting hsp105>

A motif binding to HLA-A24, for which 60% of Japanese people get positive, is almost identical to a motif, to which $K^d$ of a BALB/c mouse binds. A peptide that is shared by human hsp105 and mouse hsp105 and is predicted to bind to both HLA-A24 and $K^d$ is selected from the sequence of hsp105, using HLA-peptide binding prediction (http://bimas/dcrt.nih.gov/molbio/hla_bind/). Nine types of peptides consisting of 9 or 10 amino acids were synthesized by the Fmoc/PyBOP method. The sequences of the peptides and the estimated binding values to $K^d$ are shown in Table 2.

TABLE 2 hsp 105-derived peptides

| No. | Position | Sequence | | Binding Score |
|---|---|---|---|---|
| 1 | hsp105 180-188 | NYGIYKQDL | (SEQ ID NO: 3) | 2400 |
| 2 | hsp105 214-223 | AFNKGKLKVL | (SEQ ID NO: 4) | 960 |
| 3 | hsp105 251-260 | KYKLDAKSKI | (SEQ ID NO: 5) | 2880 |
| 4 | hsp105 305-313 | QFEELCAEL | (SEQ ID NO: 6) | 1382 |
| 5 | hsp105 433-442 | TFLRRGPFEL | (SEQ ID NO: 8) | 1920 |
| 6 | hsp105 570-579 | MYIETEGKMI | (SEQ ID NO: 7) | 4800 |
| 7 | hsp105 597-606 | ECVYEFRDKL | (SEQ ID NO: 23) | 80 |
| 8 | hsp105 682-690 | HYAKIAADF | (SEQ ID NO: 10) | 60 |
| 9 | hsp105 696-705 | KYNHIDESEM | (SEQ ID NO: 11) | 432 |

Example 3

DNA Vaccine

Plasmid DNA produced by incorporating mouse hsp105 cDNA into an expression vector pCAGGS was adjusted to be a suitable concentration. It was then used as a vaccine for the following performance evaluation test. With regard to this mouse hsp105-pCAGGS DNA vaccine, *Escherichia coli* was cultured, and thereafter, plasmid DNA was extracted from the *Escherichia coli* and purified, so as to produce the vaccine in large scale.

<Anti-Cancer Effects of Peptide Vaccine and DNA Vaccine>

The following samples were injected into the muscle of each BALB/c mouse: (1) a normal saline solution, (2) only a vector, (3) a hsp105 cDNA vector, (4) only an adjuvant, (5) an adjuvant+a peptide. Thereafter, a colon cancer cell line Colon-26 derived from a syngeneic mouse, that highly expresses hsp105, was subcutaneously transplanted into the back of the mouse. Thereafter, the development of the cancer in the mice was evaluated in the following points: (1) the area of a cancerous portion, (2) the ratio of mice in which the cancer developed, and (3) the ratio of surviving mice. The results are shown in FIGS. 3A, 3B, and 3C.

Figure 3:
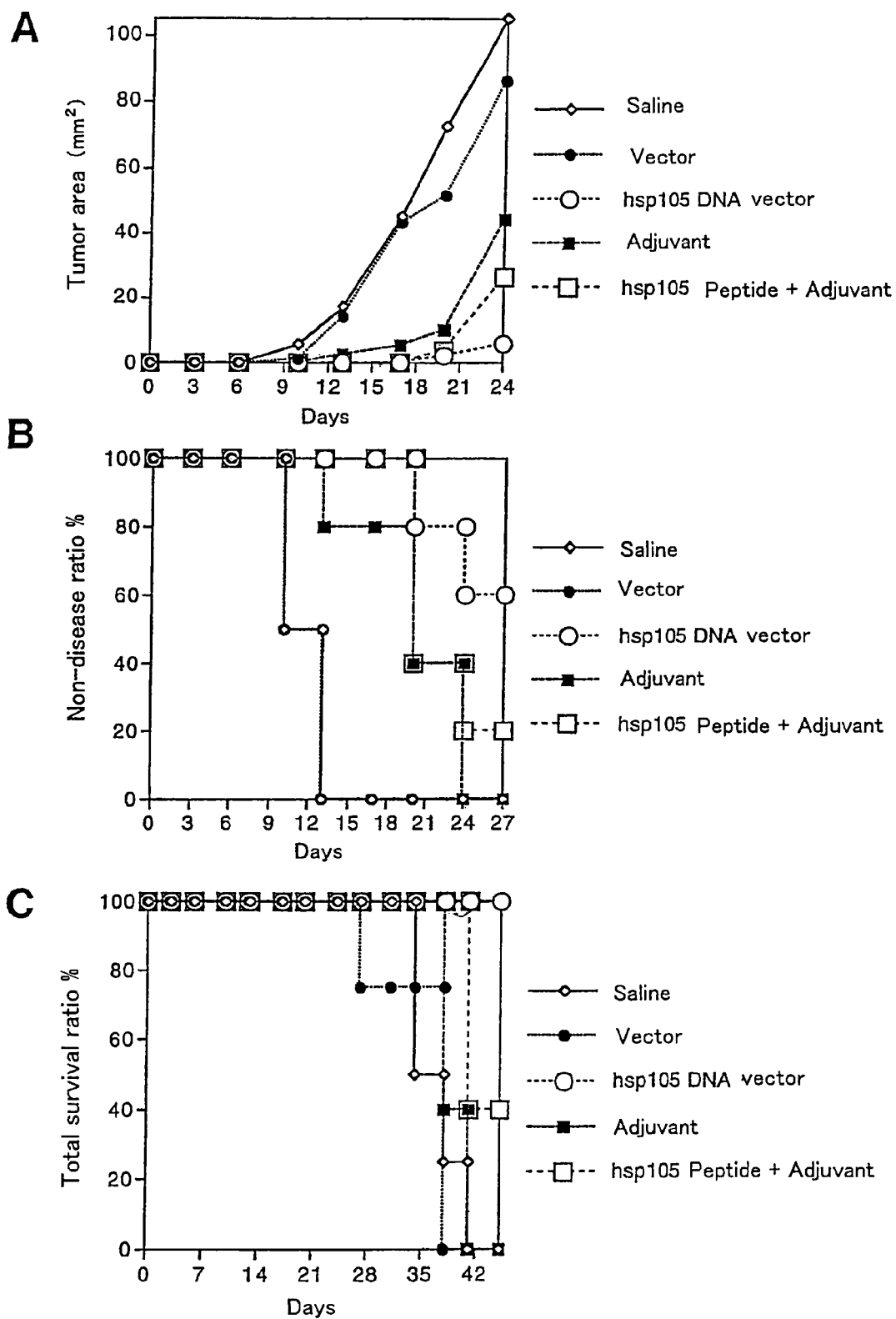
FIG. 3 is a graph showing the anticancer effects of an hsp105 DNA vaccine, an hsp105 peptide vaccine, and a control on mouse colon cancer cells Colon-26. A represents the area of a cancerous portion, B represents the ratio of mice wherein the cancer has developed, and C represents the ratio of surviving mice.

As shown in FIGS. 3A, 3B, and 3C, when $3 \times 10^4$ cells of Colon-26 were transplanted, until 13 days after the immunization, a tumor developed in all the 5 mice immunized with a normal saline solution and in all the 5 mice immunized with only pCAGGS. On the other hand, in the case of 5 mice immunized with hsp105-DNA vaccine, a tumor developed in one mouse 20 days after the immunization and in another mouse 24 days after the immunization. However, the remaining 3 mice completely rejected the development of a tumor. In the case of the adjuvant administration group, a tumor developed in all the 5 mice until 24 days after the immunization. There were observed significant differences between the DNA vaccine-, peptide vaccine-, and adjuvant-administration groups, and the normal saline solution- and vector-administration groups (FIG. 3B). The same results were obtained regarding the mean tumor area (FIG. 3A).

From these results, it is clear that the peptide vaccine and the DNA vaccine have the effects as anticancer agents. Considering a survival curve, 2 out of the 5 mice still survived 45 days after the immunization in the normal saline solution-, vector-, and adjuvant-administration groups. Moreover, all the 5 mice survived in the DNA vaccine-administration group. The DNA vaccine group had significant differences from the other 4 groups. The peptide vaccine group had a significantly longer survival period than those of the normal saline solution-, vector-, and adjuvant-administration groups (FIG. 3C). Furthermore, the mice that rejected the development of a tumor were pathologically observed, and it was confirmed that there were no damage on normal organs and that a large number of inflammatory cells filtrated into sites that rejected the development of a tumor.

<Determination of CTL Epitope Peptide of hsp105>

Figure 4:
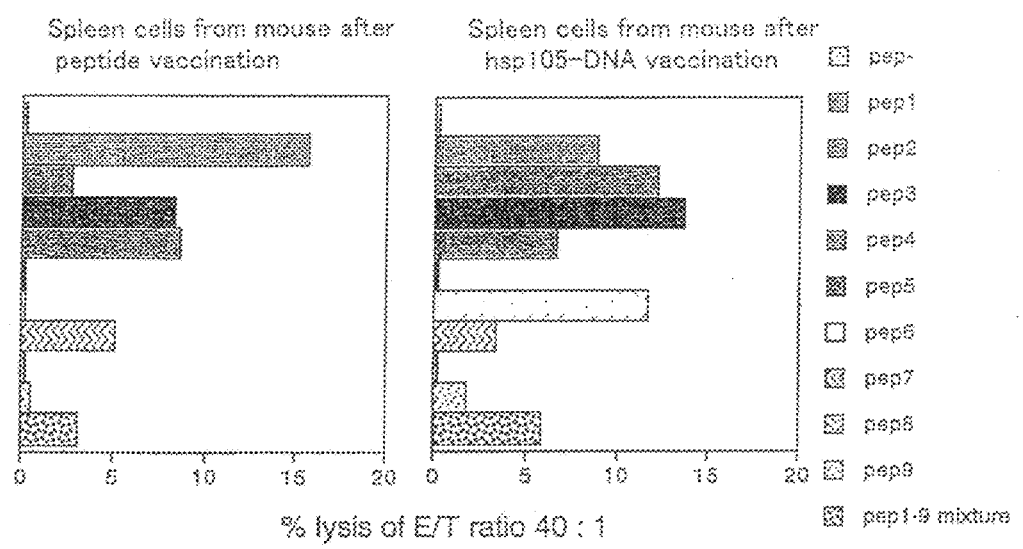
FIG. 4 is a graph showing the results obtained by measuring by $^{51}$Cr release assay, the cytotoxic activities on Colon-26 of various types of peptide vaccines derived from hsp105 proteins, or the cytotoxic activities of DNA vaccines encoding such hsp105 proteins.

In order to identify a CTL epitope peptide, pancreatic cells were recovered from the mice, on which the DNA vaccine-peptide vaccine had worked. The recovered cells were stimulated once with the 9 types of peptides shown in Table 2, and the cytotoxic activity on Colon-26 was analyzed by $^{51}$Cr release assay. As a result, it was found that among the above-described 9 types of peptides, the following 5 types of peptides 1, 2, 3, 4, and 5 are useful (FIG. 4).

```
                                             (SEQ ID NO: 3)
    Asn-Tyr-Gly-Ile-Tyr-Lys-Gln-Asp-Leu         (1)

(SEQ ID NO: 4)
    Ala-Phe-Asn-Lys-Gly-Lys-Leu-Lys-Val-Leu    (2)

(SEQ ID NO: 5)
    Lys-Tyr-Lys-Leu-Asp-Ala-Lys-Ser-Lys-Ile    (3)

(SEQ ID NO: 6)
    Gln-Phe-Glu-Glu-Leu-Cys-Ala-Glu-Leu        (4)

(SEQ ID NO: 7)
    Met-Tyr-Ile-Glu-Thr-Glu-Gly-Lys-Met-Ile    (5)
```

<Agent for Diagnosing Cancers>

Using an hsp105 antibody, the pathological diagnosis of the following cancers can be conducted: pancreatic cancer, colon cancer, brain tumor, malignant melanoma, chronic myelocytic leukemia, acute myelocytic leukemia, lymphoma, esophageal cancer, kidney cancer, prostatic cancer, lung cancer, breast cancer, stomach cancer, hepatic cancer, gallbladder cancer, testicular cancer, uterine cancer, ovarian cancer, thyroid cancer, bladder cancer, and sarcoma.

<CTL Cancer Therapeutic Agent>

In the case of mice, it was clarified that killer T cells recognizing hsp105 and/or a peptide constituting the hsp105 as an antigen do not impair normal cells and have cytotoxic activity only on mouse colon cancer. Thus, there is a possibility that CTL can be used as a cancer therapeutic or preventive agent with few side effects in human pancreatic and colon cancers wherein hsp105 is highly expressed.

Example 4

Identification of CTL Epitope Peptide of HLA-A24 of hsp105 in Human

In order to determine the CTL epitope peptide of HLA-A24 of hsp105 in human, the peripheral blood lymphocytes collected from two colon cancer patients with HLA-A24 were stimulated 4 times with 9 types of peptides shown in Table 3. Thereafter, the cytotoxic activity on a human colon cancer cell line sw620, which highly expresses hsp105 and also expresses HLA-A24, was analyzed by $^{51}$Cr release assay.

Specifically, monocytes were separated from the peripheral blood. Two millions of monocytes per well on a 24-well plate were cultured in 2 ml of a culture solution containing 10% autoserum, IL-2 (100 IU/ml), and 10 µM each peptide for 1 week. Thereafter, every week, the above culture product was stimulated with 200,000 dendritic cells (DC), which had been induced over 1 week, pulsed with 10 mM the above peptide and exposed to radioactive rays, repeatedly 3 times. 6 days later, the cytotoxic activity thereof was analyzed. Herein, two millions of monocytes were cultured in the presence of GM-CSF (100 ng/ml) and IL-4 (100 U/ml) for 5 days, and TNF-α (20 ng/ml) was further added thereto, followed by culture for 2 days. The obtained culture product was used as DC.

CTL which impairs C1RA2402 cells stimulated with the above peptide rather than those that were not stimulated with the above peptide was defined as peptide-specific positive. The results are shown in Table 3. The boldface figures in Table 3 indicate that CTL that is specific for the peptide and has cancer cell cytotoxicity can be induced.

TABLE 3

Peptides which can induce peptide-specific and cancer cell cytotoxic killer T cell by stimulating human peripheral blood lymphocytes of HLA-A24

| hsp105-derived peptide | Position | Sequence | HLA-A2402-binding score | Each peptide-induced CTLs from Pt 1 (HLA-A2402/) % Lysis to | | | Each peptide-induced CTLs from Pt 2 (HLA-A2402/) % Lysis to | | |
|---|---|---|---|---|---|---|---|---|---|
| | | | | sw620 (HLA-A 0201/2402) | C1RA2402 | C1RA2402 peptide 10µM | sw620 (HLA-A0201) | C1RA2402 | C1RA2402 peptide 10µM |
| A24-1 | 180-188 | NYGIYKQDL (SEQ ID NO: 3) | 240 | 16 | 42 | 31 | 32 | 13 | 25 |
| A24-2 | 214-223 | AFNKGKLKVL (SEQ ID NO: 4) | 30 | 0 | 42 | 49 | 40 | 28 | 54 |
| A24-3 | 251-260 | KYKLDAKSKI (SEQ ID NO: 5) | 110 | 50 | 29 | 46 | 21 | 33 | 44 |
| A24-4 | 305-313 | QFEELCAEL (SEQ ID NO: 6) | 48 | 48 | 22 | 43 | 16 | 40 | 38 |
| A24-5 | 433-442 | TFLRRGPFEL (SEQ ID NO: 8) | 33 | 53 | 33 | 33 | 26 | 33 | 46 |
| A24-6 | 613-622 | MYIETEGKMI (SEQ ID NO: 7) | 90 | 49 | 22 | 47 | 29 | 28 | 52 |
| A24-7 | 640-649 | EYVYEFRDKL (SEQ ID NO: 9) | 330 | 40 | 22 | 45 | 8 | 26 | 31 |
| A24-8 | 725-733 | HYAKIAADF (SEQ ID NO: 10) | 140 | 41 | 25 | 37 | 66 | 28 | 43 |
| A24-9 | 739-748 | KYNHIDESEM (SEQ ID NO: 11) | 83 | 19 | 36 | 43 | 33 | 24 | 45 |

Example 5

Identification of CTL Epitope Peptide of HLA-A2 of hsp105 in Human

In order to determine the CTL epitope peptide of HLA-A2 of hsp105 in human, the peripheral blood lymphocytes of a colon cancer patient with HLA-A2 and those of a healthy subject with HLA-2 were stimulated 4 times with 30 types of peptides shown in Table 4. Thereafter, the cytotoxic activity on a human colon cancer cell line sw620, which highly expresses hsp105 and also expresses HLA-A2, was analyzed. Specific experimental methods were the same as those in Example 4.

In addition, sw620 cells, the expression level of hsp105 of which was reduced by RNAi, was defined as sw620 hsp105-RNAi cells. If CTL did not impair the sw620 hsp105-RNAi cells, then it was judged that it had cytotoxic activity specific for hsp105. Moreover, CTL impairing sw620 hsp105-RNAi cells stimulated with the above peptide rather than those that were not stimulated with the above peptide was defined as peptide-specific positive. The results are shown in Table 4. The boldface figures in Table 4 indicate that CTL that is specific for the peptide and has cancer cell cytotoxicity can be induced.

TABLE 4

Peptides which can induce peptide-specific and cancer cell cytotoxic killer T cell by stimulating peripheral blood lymphocytes of HLA-A2. Sequences A2-1 to A2-7, A2-9, A2-10, A2-14, A2-16 to A2-19, A2-21, A2-22, A2-24, A2-28, and A2-29 are as disclosed in SEQ ID NO: 1.

| hsp105-derived peptide | Position | Sequence | HLA-A2401-binding score | each peptide-induced CTLs from Pt 1 (HLA-A0207/3301) % Lysis to | | | each peptide-induced CTLs from HD 1 (HLA-A0201/0207) % Lysis to | | |
|---|---|---|---|---|---|---|---|---|---|
| | | | | sw620 (HLA-0201) | sw620 hsp105-RNAi | sw620 hsp-105 RNAi peptide 10 µM | sw620 (HLA-A0201) | sw620 hsp105-RNAi | sw620 hsp105-RNAi peptide 10 µM |
| A2-1 | 86-94 | NLSYDLVPL (SEQ ID NO: 31) | 49 | 5 | 68 | 56 | — | — | — |
| A2-2 | 103-111 | VMYMGEEHL (SEQ ID NO: 32) | 41 | 20 | 41 | 36 | — | — | — |
| A2-3 | 105-114 | YMGEEHLFSV (SEQ ID NO: 33) | 12637 | 5 | 0 | 0 | — | — | — |
| A2-4 | 120-128 | MLLTKLKET (SEQ ID NO: 34) | 107 | 0 | 0 | 1 | 6 | 35 | 3 |
| A2-5 | 141-149 | VISVPSFFT (SEQ ID NO: 24) | 55 | 4 | 0 | 5 | — | — | — |
| A2-6 | 155-163 | SVLDAAQIV (SEQ ID NO: 25) | 37 | 5 | 7 | 18 | 4 | 0 | 13 |
| A2-7 | 169-177 | RLMNDMTAV (SEQ ID NO: 26) | 591 | 4 | 0 | 8 | 2 | 29 | 32 |
| A2-8 | 190-199 | SLDEKPRIVV (SEQ ID NO: 12) | 46 | 30 | 18 | 0 | 26 | 9 | 40 |
| A2-9 | 202-210 | DMGHSAFQV (SEQ ID NO: 27) | 21 | 26 | 0 | 3 | — | — | — |
| A2-10 | 222-231 | VLGTAFDPFL (SEQ ID NO: 35) | 759 | 0 | 29 | 20 | 2 | 0 | 0 |
| A2-11 | 265-273 | RLYQECEKL (SEQ ID NO: 13) | 33 | 18 | 0 | 28 | 15 | 0 | 17 |
| A2-12 | 275-284 | KLMSSNSTDL (SEQ ID NO: 14) | 276 | 10 | 1 | 13 | 10 | 28 | 58 |
| A2-13 | 276-284 | LMSSNSTDL (SEQ ID NO: 15) | 26 | 11 | 0 | 21 | 11 | 0 | 14 |
| A2-14 | 300-309 | KMNRSQFEEL (SEQ ID NO: 36) | 50 | 11 | 0 | 0 | 44 | 61 | 9 |
| A2-15 | 304-313 | SQFEELCAEL (SEQ ID NO: 16) | 32 | 12 | 0 | 4 | 21 | 0 | 9 |
| A2-16 | 313-321 | LLQKIEVPL (SEQ ID NO: 37) | 36 | 10 | 21 | 8 | — | — | — |

TABLE 4-continued

Peptides which can induce peptide-specific and cancer cell cytotoxic killer T cell by stimulating peripheral blood lymphocytes of HLA-A2. Sequences A2-1 to A2-7, A2-9, A2-10, A2-14, A2-16 to A2-19, A2-21, A2-22, A2-24, A2-28, and A2-29 are as disclosed in SEQ ID NO: 1.

| hsp105-derived peptide | Position | Sequence | HLA-A2401-binding score | each peptide-induced CTLs from Pt 1 (HLA-A0207/3301) % Lysis to | | | each peptide-induced CTLs from HD 1 (HLA-A0201/0207) % Lysis to | | |
|---|---|---|---|---|---|---|---|---|---|
| | | | | sw620 (HLA-0201) | sw620 hsp105-RNAi | sw620 hsp-105 RNAi peptide 10 μM | sw620 (HLA-A0201) | sw620 hsp105-RNAi | sw620 hsp105-RNAi peptide 10 μM |
| A2-17 | 323-332 | SLLEQTHLKV (SEQ ID NO: 38) | 1055 | 1 | 76 | 34 | 32 | 0 | 0 |
| A2-18 | 381-389 | AILSPAFKV (SEQ ID NO: 39) | 205 | 50 | 0 | 0 | 22 | 28 | 9 |
| A2-19 | 434-442 | FLRRGPFEL (SEQ ID NO: 40) | 43 | 8 | 39 | 3 | — | — | — |
| A2-20 | 458-467 | KIGRFVVQNV (SEQ ID NO: 17) | 76 | 24 | 0 | 9 | 32 | 9 | 4 |
| A2-21 | 601-610 | NLVWQLGKDL (SEQ ID NO: 28) | 21 | 7 | 0 | 4 | 5 | 0 | 4 |
| A2-22 | 602-610 | LVWQLGKDL (SEQ ID NO: 29) | 26 | 19 | 0 | 3 | — | — | — |
| A2-23 | 641-649 | YVYEFRDKL (SEQ ID NO: 18) | 210 | 26 | 2 | 13 | 0 | 9 | 23 |
| A2-24 | 648-657 | KLCGPYEKFI (SEQ ID NO: 30) | 200 | 9 | 0 | 0 | 42 | 0 | 9 |
| A2-25 | 668-676 | LLTETEDWL (SEQ ID NO: 19) | 401 | 32 | 0 | 27 | 23 | 42 | 27 |
| A2-26 | 675-684 | WLYEEGEDQA (SEQ ID NO: 20) | 146 | 18 | 0 | 41 | 11 | 21 | 3 |
| A2-27 | 694-702 | ELMIKIGTPV (SEQ ID NO: 21) | 19 | 14 | 0 | 13 | 22 | 0 | 0 |
| A2-28 | 714-723 | KMFEELGQRL (SEQ ID NO: 41) | 819 | 11 | 2 | 0 | 5 | 0 | 0 |
| A2-29 | 757-765 | EVMEWMNNV (SEQ ID NO: 42) | 15 | 1 | 0 | 0 | — | — | — |
| A2-30 | 765-774 | VMNAQAKKSL (SEQ ID NO: 22) | 26 | 0 | 0 | 11 | 26 | 0 | 12 |

Example 6

Results of Immunohistochemical Analysis of hsp105 in Tissues

The expression of hsp105 in various tissues was immunohistochemically analyzed. Specifically, thin sections with a size of 3 mm were prepared from blocks obtained by immobilizing various tissues with formalin and embedding them in paraffin. Thereafter, using VECTOR stain ABC-PO (rabbit IgG) kit (Vector Laboratories, Inc. Burlingame, Calif.), these sections were subjected to immunohistochemical analysis by the ABC method (avidin-biotin complex immune peroxidase technique). Rabbit polyclonal anti-human HSP105 Ab (SAN-TACRUZ, Santa Cruz, Calif.) was purchased, and it was then 260 times diluted. The obtained product was used as a primary antibody.

Figure 5:
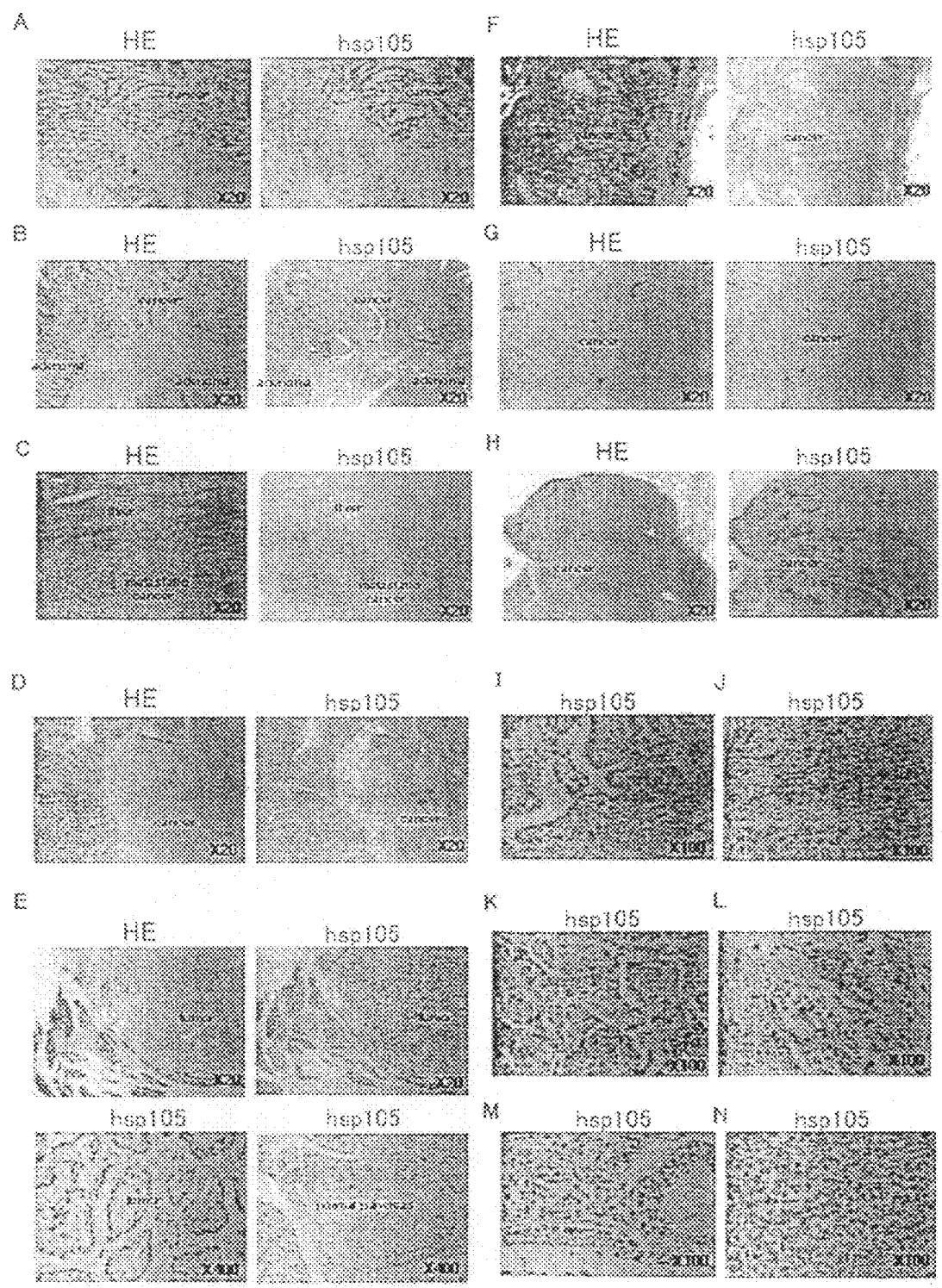
FIG. 5 shows the results of an immunohistochemical analysis on hsp105 in tissues.

FIG. 5 is a microphotograph showing the results of the above immunohistochemical analysis. In FIG. 5, symbols have the following meanings. A: colon cancer, B: colon cancer in colon polyp, C: liver metastasis of colon cancer, D: pancreatic cancer, E: insulinoma, F: papillary adenocarcinoma in breast cancer, G: scirrhus cancer in breast cancer, H: esophageal cancer, I: thyroid cancer, J: gastric malignant lymphoma, K: pheochromocytoma, L: bladder cancer, M: testis, and N: seminoma. As is clear from the results shown in FIG. 5, a high level of expression of hsp105 was observed in A, B, C, D, E, F, H, I, J, K, L, M, and N, that is, tumors other than G, and also in the testis.

Example 7

In Vivo Antitumor Activity of Mouse CD4 Positive Helper T Cell Line Induced by hsp105

Figure 6:
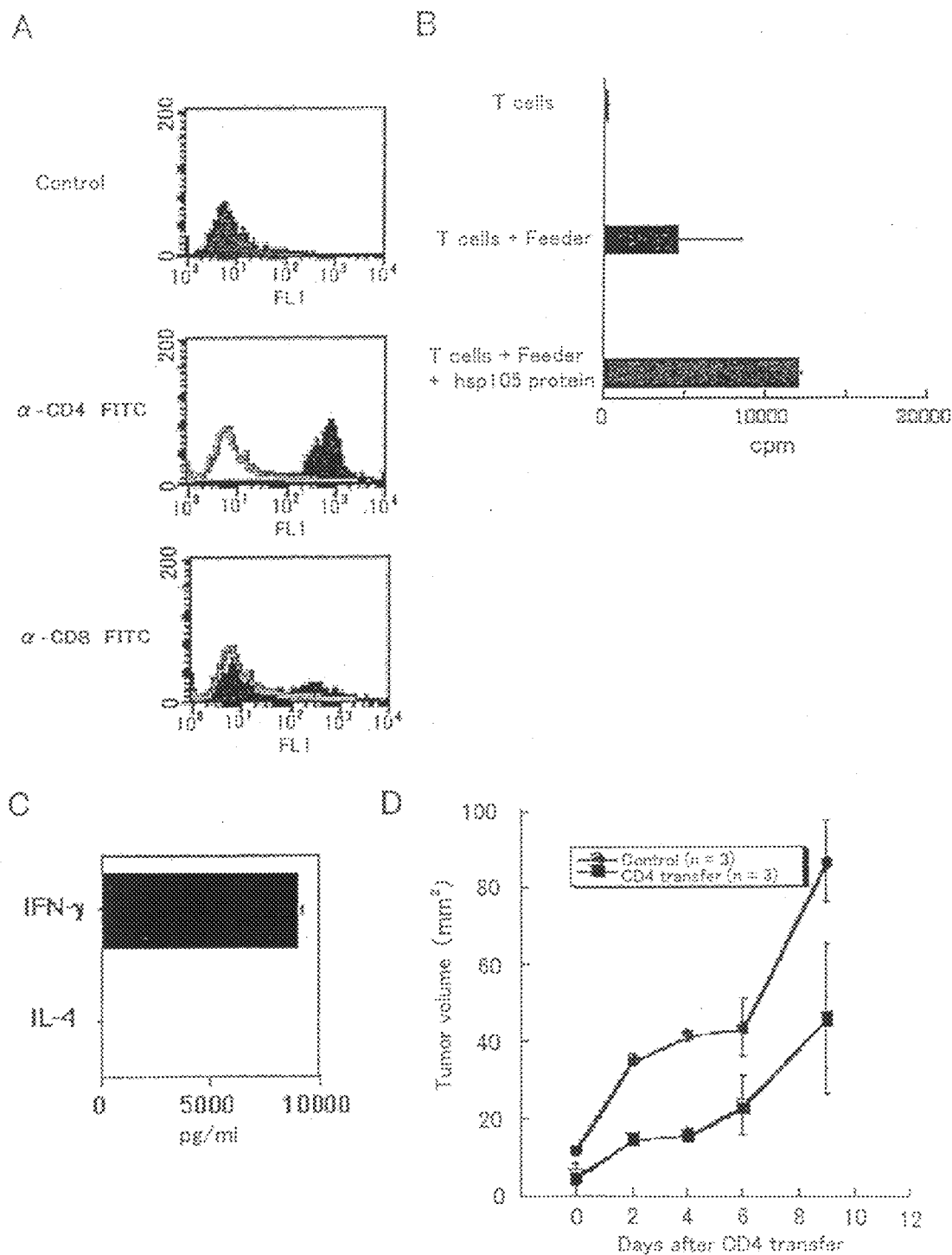
FIG. 6 shows the results obtained by analyzing the in vivo antitumor activity of a mouse CD4 positive helper T cell line induced by hsp105.

The spleen of a BALB/c mouse was collected and ground to separate spleen cells. 200,000 spleen cells per well on a 96-well flat plate were cultured in 200 μl of a culture solution containing IL-2 (100 IU/ml) and a 2 μg/ml recombinant hsp105 protein for 1 week. Thereafter, every week, the culture product was repeatedly stimulated with 200,000 spleen cells, which had been pulsed with a 2 μg/ml recombinant hsp105 protein and then exposed to radioactive rays, so as to establish multiple CD4 positive helper T cell lines (Th). The expression of CD4 and CD8 on the surface of cells was confirmed by performing immunofluorescent staining with Monoclonal Antibody MOUSE CD4-FITC, CD8-FITC (IMMUNO-TECH, Marseille, France), and then analyzed with FACS (FIG. 6A). It was examined by the intake of [$^3$H] thymidine, whether or not Th specifically reacts with the hsp105 protein and grows. Specifically, 150,000 spleen cells were placed in each well of a 96-well flat plate, and several wells were pulsed with the hsp105 protein overnight, and the other wells were not pulsed therewith. To both types of wells, 30,000 Th cells were added, followed by the reaction for 72 hours (1 μCi of [$^3$H] thymidine was added to each well for the last 16 hours). Thereafter, the intake of [$^3$H] thymidine was measured with a liquid scintillation counter. The Th cells specifically reacted with the hsp105 protein and grew (FIG. 6B). On the other hand, 24 hours after the addition of Th, the supernatant was kept. Thus, IFN-γ and IL-4 secreted from Th as a result of the reaction were measured with Mouse IFN-γ, IL-4 ELISA Ready-SET-Go! (eBioscience). The Th was of Th1 type, which generates a large amount of IFN-γ as a result of the specific reaction with the hsp105 protein (FIG. 6C). Colon-26 was subcutaneously implanted into the back of a BALB/c mouse to form a tumor with a size of 3 mm. Thereafter, the above Th was injected into the local site, followed by observation of the progression. As a result, after such a treatment, the growth of the Colon-26 tumor was clearly retarded (FIG. 6D).

From the above-described results, it was found that the BALB/c mouse CD4 positive helper T cell line induced by the hsp105 protein grows hsp105 protein-specifically, and that it delays the growth of a tumor mass of the colon cancer cell line Colon-26 that highly expresses hsp105.

Example 8

CD4 Positive Helper T Cell Line of Colon Cancer Patient Induced by hsp105

Figure 7:
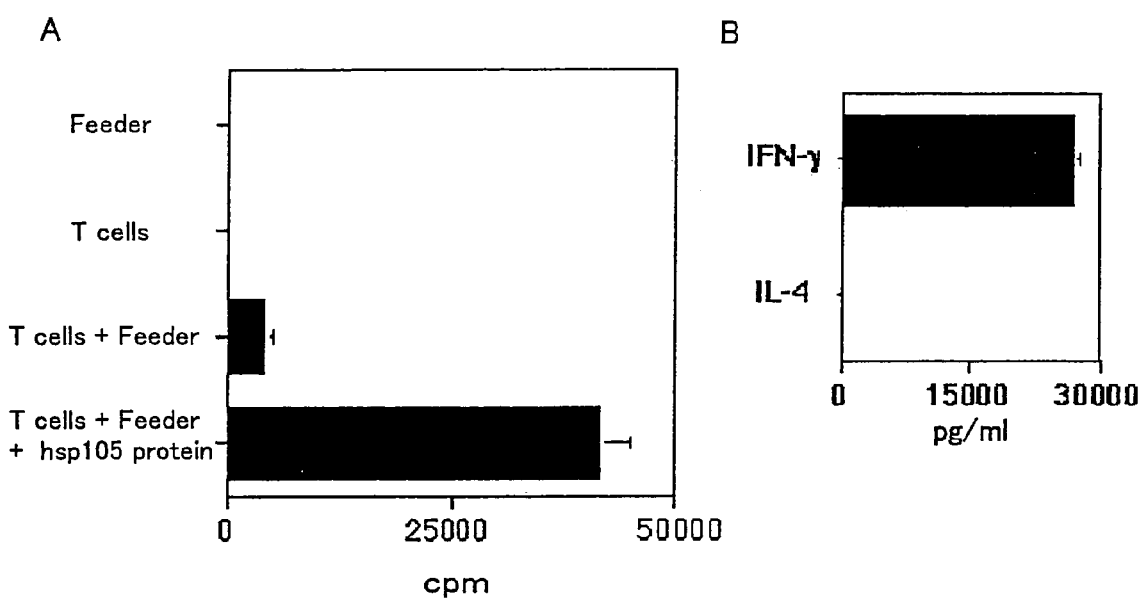
FIG. 7 shows the results obtained by inducing by hsp105, the CD4 positive helper T cell line of a patient with colon cancer.

Monocytes were separated from the peripheral blood. 200,000 monocytes per well of a 96-well flat plate were cultured in 200 μl of a culture solution containing IL-2 (100 IU/ml) and a 2 μg/ml recombinant hsp105 protein for 1 week. Thereafter, every week, the culture product was repeatedly stimulated with 200,000 monocytes, which had been pulsed with a 2 μg/ml recombinant hsp105 protein and then exposed to radioactive rays, so as to establish multiple CD4 positive helper T cell lines (Th). The expression of CD4 and CD8 on the surface of cells was confirmed by performing immunofluorescent staining using Pharmingen anti-human CD4, CD8-FITC, and then analyzed with FACS. It was examined in the same manner as in Example 7, whether or not Th specifically reacts with the hsp105 protein and grows. The Th cells specifically reacted with the hsp105 protein and grew (FIG. 7A). In addition, in the same manner as in Example 7, IFN-γ and IL-4 secreted from Th as a result of the reaction were measured using Human IFN-γ, IL-4 US ELISA Kit (BIOSOURCE, Camarillo, Calif.). The Th was of Th1 type, which generates a large amount of IFN-γ as a result of the specific reaction with the hsp105 protein (FIG. 7B). In general, it has been known that Th1 acts favorably for the induction of CTL and antitumor immunity. It was found that such Th1 can be induced also in humans by stimulating peripheral blood lymphocytes with the hsp105 protein.

Example 9

Figure 8:
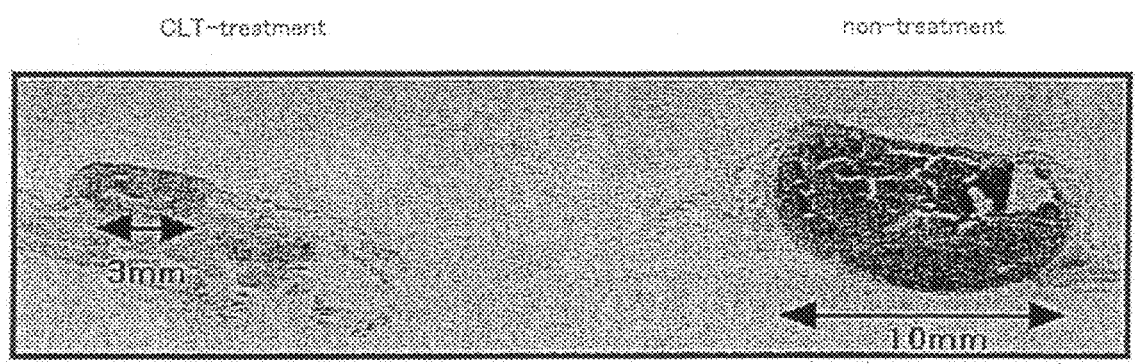
FIG. 8 shows the results obtained by examining whether or not BALB/c mouse cytotoxic T lymphocytes (CTL) induced by an hsp105-derived peptide can reduce a tumor mass of the colon cancer cell line Colon-26 which highly expresses hsp105.

In Vivo Antitumor Activity of Cytotoxic T Lymphocytes Stimulated with hsp105 Peptide It was examined whether or not BALB/c mouse cytotoxic T lymphocytes (CTL) induced by an hsp105-derived peptide Asn-Tyr-Gly-Ile-Tyr-Lys-Gln-Asp-Leu (SEQ ID NO: 3) reduce a tumor mass of the colon cancer cell line Colon-26 that highly expresses hsp105. Specifically, Colon-26 was subcutaneously implanted into the back of a BALB/c mouse to form a tumor with a size of 5 mm. Thereafter, CTL was injected into the local site. 1 week later, the mouse was subjected to anatomy, and the site was pathologically observed by HE staining. The results are shown in FIG. 8. As is apparent from the results shown in FIG. 8, the tumor was clearly reduced by administration of the CTL induced by the hsp105-derived peptide.

Also, it was examined whether or not the cytotoxic T lymphocytes (CTL) of a colon cancer patient induced by an hsp105-derived peptide Lys-Leu-Met-Ser-Ser-Asn-Ser-Thr-Asp-Leu (SEQ ID NO: 14) reduce a tumor mass of the colon cancer cell line sw620 that highly expresses hsp105. Specifically, sw620 was subcutaneously implanted into the back of a nude mouse to form a tumor with a size of 5 mm, and thereafter, CTL was injected into the local site.

Figure 9:
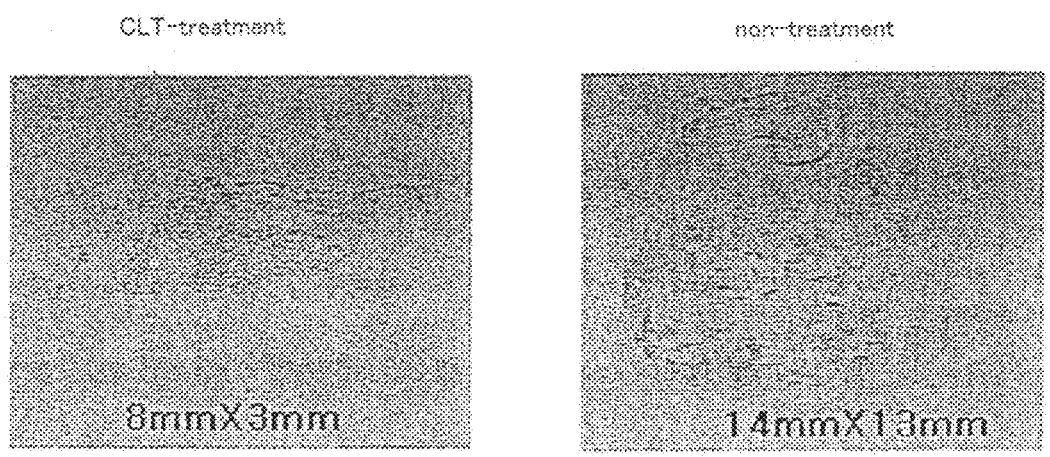
FIG. 9 shows the results obtained by examining whether or not the cytotoxic T lymphocytes (CTL) of a colon cancer patient induced by an hsp105-derived peptide can reduce a tumor mass of the colon cancer cell line sw620, which highly expresses hsp105.

1 week after injection of the CTL, the tumor was reduced. 2 weeks after the treatment, the mouse was subjected to anatomy, and the site was pathologically observed by HE staining. The results are shown in FIG. 9. As is apparent from the results shown in FIG. 9, the increase of the tumor was clearly retarded by administration of the CTL.

INDUSTRIAL APPLICABILITY

The cancer antigen protein and antigen peptide of the present invention, or DNA encoding the protein or peptide of the present invention, can be used as an excellent anti-cancer vaccine having few side effects such as self-injury. In addition, an antibody can be used as a diagnostic agent. Moreover, helper T cells, cytotoxic T lymphocytes, or an immunocyte population containing these cells, which are stimulated and activated with the antigen of the present invention, can be used as anticancer agents.

What is claimed is:

1. A cancer vaccine comprising at least one peptide consisting of the amino acid sequence shown in any one of SEQ ID NOs: 3 to 12, 14, 18 and 26, wherein the vaccine further comprises an adjuvant.

2. The cancer vaccine of claim 1 wherein the adjuvant is selected from Freund's incomplete adjuvant, BCG, trehalose dimycolate (TDM), lipopolysaccharide (LPS), alum adjuvant, and silica adjuvant.

3. A method for the treatment of cancer in a subject, wherein the cancer expresses hsp105, comprising administering to the subject the cancer vaccine of claim 1.

* * * * *

SEQUENCE LISTING

<160> NUMBER OF SEQ ID NOS: 42

<210> SEQ ID NO 1
<211> LENGTH: 858
<212> TYPE: PRT
<213> ORGANISM: Homo sapiens

<400> SEQUENCE: 1

```
Met Ser Val Val Gly Leu Asp Val Gly Ser Gln Ser Cys Tyr Ile Ala
1               5                   10                  15

Val Ala Arg Ala Gly Gly Ile Glu Thr Ile Ala Asn Glu Phe Ser Asp
                20                  25                  30

Arg Cys Thr Pro Ser Val Ile Ser Phe Gly Ser Lys Asn Arg Thr Ile
            35                  40                  45

Gly Val Ala Ala Lys Asn Gln Gln Ile Thr His Ala Asn Asn Thr Val
        50                  55                  60

Ser Asn Phe Lys Arg Phe His Gly Arg Ala Phe Asn Asp Pro Phe Ile
65                  70                  75                  80

Gln Lys Glu Lys Glu Asn Leu Ser Tyr Asp Leu Val Pro Leu Lys Asn
                85                  90                  95

Gly Gly Val Gly Ile Lys Val Met Tyr Met Gly Glu Glu His Leu Phe
                100                 105                 110

Ser Val Glu Gln Ile Thr Ala Met Leu Leu Thr Lys Leu Lys Glu Thr
            115                 120                 125

Ala Glu Asn Ser Leu Lys Lys Pro Val Thr Asp Cys Val Ile Ser Val
        130                 135                 140

Pro Ser Phe Phe Thr Asp Ala Glu Arg Arg Ser Val Leu Asp Ala Ala
145                 150                 155                 160

Gln Ile Val Gly Leu Asn Cys Leu Arg Leu Met Asn Asp Met Thr Ala
                165                 170                 175

Val Ala Leu Asn Tyr Gly Ile Tyr Lys Gln Asp Leu Pro Ser Leu Asp
                180                 185                 190

Glu Lys Pro Arg Ile Val Val Phe Val Asp Met Gly His Ser Ala Phe
            195                 200                 205

Gln Val Ser Ala Cys Ala Phe Asn Lys Gly Lys Leu Lys Val Leu Gly
        210                 215                 220

Thr Ala Phe Asp Pro Phe Leu Gly Gly Lys Asn Phe Asp Glu Lys Leu
225                 230                 235                 240

Val Glu His Phe Cys Ala Glu Phe Lys Thr Lys Tyr Lys Leu Asp Ala
                245                 250                 255

Lys Ser Lys Ile Arg Ala Leu Leu Arg Leu Tyr Gln Glu Cys Glu Lys
                260                 265                 270

Leu Lys Lys Leu Met Ser Ser Asn Ser Thr Asp Leu Pro Leu Asn Ile
            275                 280                 285

Glu Cys Phe Met Asn Asp Lys Asp Val Ser Gly Lys Met Asn Arg Ser
        290                 295                 300

Gln Phe Glu Glu Leu Cys Ala Glu Leu Leu Gln Lys Ile Glu Val Pro
305                 310                 315                 320

Leu Tyr Ser Leu Leu Glu Gln Thr His Leu Lys Val Glu Asp Val Ser
                325                 330                 335

Ala Val Glu Ile Val Gly Gly Ala Thr Arg Ile Pro Ala Val Lys Glu
                340                 345                 350

Arg Ile Ala Lys Phe Phe Gly Lys Asp Ile Ser Thr Thr Leu Asn Ala
            355                 360                 365
```

-continued

```
Asp Glu Ala Val Ala Arg Gly Cys Ala Leu Gln Cys Ala Ile Leu Ser
    370                 375                 380

Pro Ala Phe Lys Val Arg Glu Phe Ser Val Thr Asp Ala Val Pro Phe
385                 390                 395                 400

Pro Ile Ser Leu Ile Trp Asn His Asp Ser Glu Asp Thr Glu Gly Val
                405                 410                 415

His Glu Val Phe Ser Arg Asn His Ala Ala Pro Phe Ser Lys Val Leu
            420                 425                 430

Thr Phe Leu Arg Arg Gly Pro Phe Glu Leu Glu Ala Phe Tyr Ser Asp
        435                 440                 445

Pro Gln Gly Val Pro Tyr Pro Glu Ala Lys Ile Gly Arg Phe Val Val
450                 455                 460

Gln Asn Val Ser Ala Gln Lys Asp Gly Glu Lys Ser Arg Val Lys Val
465                 470                 475                 480

Lys Val Arg Val Asn Thr His Gly Ile Phe Thr Ile Ser Thr Ala Ser
                485                 490                 495

Met Val Glu Lys Val Pro Thr Glu Glu Asn Glu Met Ser Ser Glu Ala
            500                 505                 510

Asp Met Glu Cys Leu Asn Gln Arg Pro Pro Glu Asn Pro Asp Thr Asp
        515                 520                 525

Lys Asn Val Gln Gln Asp Asn Ser Glu Ala Gly Thr Gln Pro Gln Val
530                 535                 540

Gln Thr Asp Ala Gln Gln Thr Ser Gln Ser Pro Ser Pro Glu Leu
545                 550                 555                 560

Thr Ser Glu Glu Asn Lys Ile Pro Asp Ala Asp Lys Ala Asn Glu Lys
                565                 570                 575

Lys Val Asp Gln Pro Pro Glu Ala Lys Lys Pro Lys Ile Lys Val Val
            580                 585                 590

Asn Val Glu Leu Pro Ile Glu Ala Asn Leu Val Trp Gln Leu Gly Lys
        595                 600                 605

Asp Leu Leu Asn Met Tyr Ile Glu Thr Glu Gly Lys Met Ile Met Gln
    610                 615                 620

Asp Lys Leu Glu Lys Glu Arg Asn Asp Ala Lys Asn Ala Val Glu Glu
625                 630                 635                 640

Tyr Val Tyr Glu Phe Arg Asp Lys Leu Cys Gly Pro Tyr Glu Lys Phe
                645                 650                 655

Ile Cys Glu Gln Asp His Gln Asn Phe Leu Arg Leu Leu Thr Glu Thr
            660                 665                 670

Glu Asp Trp Leu Tyr Glu Gly Glu Asp Gln Ala Lys Gln Ala Tyr
        675                 680                 685

Val Asp Lys Leu Glu Glu Leu Met Lys Ile Gly Thr Pro Val Lys Val
690                 695                 700

Arg Phe Gln Glu Ala Glu Arg Pro Lys Met Phe Glu Glu Leu Gly
705                 710                 715                 720

Gln Arg Leu Gln His Tyr Ala Lys Ile Ala Ala Asp Phe Arg Asn Lys
                725                 730                 735

Asp Glu Lys Tyr Asn His Ile Asp Glu Ser Glu Met Lys Lys Val Glu
            740                 745                 750

Lys Ser Val Asn Glu Val Met Glu Trp Met Asn Asn Val Met Asn Ala
        755                 760                 765

Gln Ala Lys Lys Ser Leu Asp Gln Asp Pro Val Val Arg Ala Gln Glu
770                 775                 780

Ile Lys Thr Lys Ile Lys Glu Leu Asn Asn Thr Cys Glu Pro Val Val
```

```
                    785                 790                 795                 800
Thr Gln Pro Lys Pro Lys Ile Glu Ser Pro Lys Leu Glu Arg Thr Pro
                805                 810                 815

Asn Gly Pro Asn Ile Asp Lys Lys Glu Glu Asp Leu Glu Asp Lys Asn
                820                 825                 830

Asn Phe Gly Ala Glu Pro Pro His Gln Asn Gly Glu Cys Tyr Pro Asn
                835                 840                 845

Glu Lys Asn Ser Val Asn Met Asp Leu Asp
                850                 855

<210> SEQ ID NO 2
<211> LENGTH: 3611
<212> TYPE: DNA
<213> ORGANISM: Homo sapiens

<400> SEQUENCE: 2
gaggaagtgg gacctcccct tttgggtcgg tagttcagcg ccggcgccgg tgtgcgagcc    60
gcggcagagt gaggcaggca acccgaggtg cggagcgacc tgcggaggct gagccccgct   120
ttctcccagg gtttcttatc agccagccgc cgctgtcccc ggggggagtag gaggctcctg   180 acaggccgcg gctgtctgtg tgtccttctg agtgtcagag aacggccag accccgcggg    240 ccggagcaga acgcggccag ggcagaaagc ggcggcagga aagcaggca ggggggccgga   300 ggacgcagac cgagacccga ggcggaggcg gaccgcgagc cggccatgtc ggtggtgggg   360
ttggacgtgg gctcgcagag ctgctacatc gcggtagccc gggccggggg catcgagacc   420
atcgccaatg agttcagcga ccggtgcacc ccgtcagtca tatcatttgg atcaaaaaat   480
agaacaatcg gagttgcagc caaaaatcag caaatcactc atgcaaacaa tacggtgtct   540
aacttcaaaa gatttcatgg ccgagcattc aacgaccct tcattcaaaa ggagaaggaa    600
aacttgagtt acgatttggt tccattgaaa atggtggag ttggaataaa ggtaatgtac    660
atgggtgaag aacatctatt tagtgtggag cagataacag ccatgttgtt gactaagctg    720
aaggaaactg ctgaaaacag cctcaagaaa ccagtaacag attgtgttat ttcagtcccc    780 tccttctttta cagatgctga gaggcgatct gtgttagatg ctgcacagat tgttggccta    840
aactgtttaa gacttatgaa tgacatgaca gctgttgctt tgaattacgg aatttataag    900
caggatctcc caagcctgga tgagaaacct cggatagtgg ttttttgttga tatgggacat   960 tcagcttttc aagtgtctgc ttgtgctttt aacaagggaa aattgaaggt actgggaaca  1020
gcttttgatc ctttcttagg aggaaaaaac ttcgatgaaa agttagtgga acatttctgt  1080
gcagaattta aaactaagta caagttggat gcaaaatcca aaatacgagc actcctacgt  1140
ctgtatcagg aatgtgaaaa actgaaaaag ctaatgagct ctaacagcac agaccttcca  1200
ctgaatatcg aatgctttat gaatgataaa gatgtttccg gaaagatgaa caggtcacaa  1260
tttgaagaac tctgtgctga acttctgcaa aagatagaag tacccctta ttcactgttg  1320 gaacaaactc atctcaaagt agaagatgtg agtgcagttg agattgttgg aggcgctaca  1380
cgaattccag ctgtgaagga agaattgcc aaattctttg gaaagatat tagcacaaca  1440 ctcaatgcag atgaagcagt agccagagga tgtgcattac agtgtgcaat acttcccccg  1500
gcatttaaag ttagagaatt ttccgtcaca gatgcagttc ctttccaat atctctgatc  1560 tggaaccatg attcagaaga tactgaaggt gttcatgaag tctttagtcg aaaccatgct  1620 gctccttttct ccaagttct caccttttctg agagggggc cttttgagct agaagctttc  1680
tattctgatc cccaaggagt tccatatcca gaagcaaaaa taggccgctt tgtagttcag  1740
```

```
aatgtttctg cacagaaaga tggagaaaaa tctagagtaa aagtcaaagt gcgagtcaac    1800
acccatggca ttttcaccat ctctacggca tctatggtgg agaaagtccc aactgaggag    1860
aatgaaatgt cttctgaagc tgacatggag tgtctgaatc agagaccacc agaaaaccca    1920
gacactgata aaaatgtcca gcaagacaac agtgaagctg aacacagcc ccaggtacaa     1980 actgatgctc aacaaacctc acagtctccc ccttcacctg aacttacctc agaagaaaac    2040
aaaatcccag atgctgacaa agcaaatgaa aaaaagttg accagcctcc agaagctaaa     2100
aagcccaaaa taaaggtggt gaatgttgag ctgcctattg aagccaactt ggtctggcag    2160
ttagggaaag accttcttaa catgtatatt gagacagagg gtaagatgat aatgcaagat    2220
aaattggaaa agaaaggaa tgatgctaaa aatgcagttg aggaatatgt gtatgagttc     2280
agagacaagc tgtgtggacc atatgaaaaa tttatatgtg agcaggatca tcaaaatttt    2340
ttgagactcc tcacagaaac tgaagactgg ctgtatgaag aaggagagga ccaagctaaa    2400
caagcatatg ttgacaagtt ggaagaatta atgaaaattg cactccagt taaagttcgg     2460 tttcaggaag ctgaagaacg gccaaaaatg tttgaagaac taggacagag gctgcagcat    2520
tatgccaaga tagcagctga cttcagaaat aaggatgaga atacaaccaa tattgatgag    2580
tctgaaatga aaaagtgga gaagtctgtt aatgaagtga tggaatggat gaataatgtc     2640
atgaatgctc aggctaaaaa gagtcttgat caggatccag ttgtacgtgc tcaggaaatt    2700
aaaacaaaaa tcaaggaatt gaacaacaca tgtgaacccg ttgtaacaca accgaaacca    2760
aaaattgaat cacccaaact ggaaagaact ccaaatggcc caaatattga taaaaaggaa    2820
gaagatttag aagacaaaaa caattttggt gctgaacctc cacatcagaa tggtgaatgt    2880
taccctaatg agaaaaattc tgttaatatg gacttggact agataacctt aaattggcct    2940
attccttcaa ttaataaaat attttttgcca tagtatgtga ctctacataa catactgaaa   3000
ctatttatat tttctttttt aaggatattt agaaattttg tgtattatat ggaaaaagaa    3060
aaaaagctta agtctgtagt ctttatgatc ctaaagggaa aaattgcctt ggtaactttc    3120
agattcctgt ggaattgtga attcatacta agctttctgt gcagtctcac catttgcatc    3180
actgaggatg aaactgactt ttgtcttttg gagaaaaaaa actgtactgt tgttcaagag    3240
ggctgtgatt aaaatcttta agcatttgtt cctgccaagg tagttttctt gcattttgct    3300
ctccattcag catgtgtgtg ggtgtggatg tttataaaca agactaagtc tgacttcata    3360
agggctttct aaaaccattt ctgtccaaga gaaatgact ttttgctttg atattaaaaa      3420
ttcaatgagt aaaacaaaag ctagtcaaat gtgttagcag catgcagaac aaaaactta     3480 aactttctct ctcactatac agtatattgt caatgtgaaa gtgtggaatg aagaaatgt     3540 cgatcctgtt gtaactgatt gtgaacactt ttatgagctt taaaataaag ttcatcttat    3600
ggtgtcattt t                                                          3611
```

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Tyr Gly Ile Tyr Lys Gln Asp Leu
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Phe Asn Lys Gly Lys Leu Lys Val Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Tyr Lys Leu Asp Ala Lys Ser Lys Ile
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Phe Glu Glu Leu Cys Ala Glu Leu
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Tyr Ile Glu Thr Glu Gly Lys Met Ile
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Leu Arg Arg Gly Pro Phe Glu Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

Glu Tyr Val Tyr Glu Phe Arg Asp Lys Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Tyr Ala Lys Ile Ala Ala Asp Phe
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Tyr Asn His Ile Asp Glu Ser Glu Met
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Leu Asp Glu Lys Pro Arg Ile Val Val
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Leu Tyr Gln Glu Cys Glu Lys Leu
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Leu Met Ser Ser Asn Ser Thr Asp Leu
1               5                   10

<210> SEQ ID NO 15
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

Leu Met Ser Ser Asn Ser Thr Asp Leu
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Phe Glu Glu Leu Cys Ala Glu Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ile Gly Arg Phe Val Val Gln Asn Val
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Val Tyr Glu Phe Arg Asp Lys Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Thr Glu Thr Glu Asp Trp Leu
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Leu Tyr Glu Glu Gly Glu Asp Gln Ala
1               5                   10
```

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Leu Met Lys Ile Gly Thr Pro Val
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Met Asn Ala Gln Ala Lys Lys Ser Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Cys Val Tyr Glu Phe Arg Asp Lys Leu
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Ile Ser Val Pro Ser Phe Phe Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Val Leu Asp Ala Ala Gln Ile Val
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Arg Leu Met Asn Asp Met Thr Ala Val
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Met Gly His Ser Ala Phe Gln Val
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Leu Val Trp Gln Leu Gly Lys Asp Leu
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Val Trp Gln Leu Gly Lys Asp Leu
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Leu Cys Gly Pro Tyr Glu Lys Phe Ile
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Leu Ser Tyr Asp Leu Val Pro Leu
1               5

<210> SEQ ID NO 32
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Met Tyr Met Gly Glu Glu His Leu
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Met Gly Glu Glu His Leu Phe Ser Val
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Leu Leu Thr Lys Leu Lys Glu Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Leu Gly Thr Ala Phe Asp Pro Phe Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Met Asn Arg Ser Gln Phe Glu Glu Leu
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Leu Gln Lys Ile Glu Val Pro Leu
```

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Leu Leu Glu Gln Thr His Leu Lys Val
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ile Leu Ser Pro Ala Phe Lys Val
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Leu Arg Arg Gly Pro Phe Glu Leu
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Met Phe Glu Glu Leu Gly Gln Arg Leu
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Val Met Glu Trp Met Asn Asn Val
1               5